United States Patent
Antony

(10) Patent No.: US 12,251,415 B1
(45) Date of Patent: Mar. 18, 2025

(54) CURCUMINOID COMPOSITION OF CURCUMIN-KETO, METHOD OF PREPARATION AND USE THEREOF

(71) Applicant: ARJUNA NATURAL PRIVATE LIMITED, Alwaye (IN)

(72) Inventor: Benny Antony, Angamaly (IN)

(73) Assignee: ARJUNA NATURAL PRIVATE LIMITED, Alwaye (IN)

( * ) Notice: Subject to any disclaimer, the term of this patent is extended or adjusted under 35 U.S.C. 154(b) by 0 days.

(21) Appl. No.: 18/796,479

(22) Filed: Aug. 7, 2024

Related U.S. Application Data

(63) Continuation of application No. PCT/IB2024/055537, filed on Jun. 6, 2024.

(30) Foreign Application Priority Data

Jan. 18, 2024  (IN) .............................. 202441003735
May 16, 2024  (IN) .............................. 202441003735

(51) Int. Cl.
*A61K 36/9066* (2006.01)
*A61K 31/12* (2006.01)

(52) U.S. Cl.
CPC .......... *A61K 36/9066* (2013.01); *A61K 31/12* (2013.01)

(58) Field of Classification Search
None
See application file for complete search history.

(56) References Cited

U.S. PATENT DOCUMENTS

| | | |
|---|---|---|
| 7,736,679 B2 | 6/2010 | Antony |
| 7,879,373 B2 | 2/2011 | Antony |
| 7,883,728 B2 | 2/2011 | Antony |
| 8,153,172 B2 | 4/2012 | Antony |
| 8,197,869 B2 | 6/2012 | Antony |
| 8,329,233 B2 | 12/2012 | Antony |
| 8,623,431 B2 | 1/2014 | Antony |
| 8,859,020 B1 | 10/2014 | Antony |
| 8,895,087 B2 | 11/2014 | Antony |
| 8,993,013 B2 | 3/2015 | Antony |
| 9,492,402 B2 * | 11/2016 | Antony ................. A61K 31/12 |
| 9,861,677 B2 | 1/2018 | Antony |
| 9,878,040 B2 | 1/2018 | Antony |
| 10,159,654 B2 | 12/2018 | Antony |
| 10,286,027 B2 | 5/2019 | Antony |
| 10,485,843 B2 | 11/2019 | Antony |
| 10,512,616 B2 | 12/2019 | Antony |
| 10,543,277 B2 | 1/2020 | Antony et al. |

FOREIGN PATENT DOCUMENTS

| | | |
|---|---|---|
| EP | 2555787 | 11/2017 |
| EP | 1890546 | 11/2018 |
| IN | 200430 | 5/2006 |
| IN | 321323 | 9/2019 |
| IN | 528344 | 3/2024 |
| JP | 5039032 | 10/2012 |
| JP | 5511895 | 6/2014 |

OTHER PUBLICATIONS

Kawano, SI, Inohana, Y, Hashi, Y, Lin, JM, Analysis of keto-enol tautomers of curcumin by liquid chromatography/mass spectroscopy, Chinese Chemical Letters 24 (2013) 685-687.
Rege, SA, Arya, M, Momin, SA, Structure activity relationship of tautomers of curcumin: a review, Ukrainian food journal, vol. 8. Issue 1: p. 45-60, 2019.
Manolova, Y, Deneva, V, Antonov, L, Drakalska, E, Momekova, D, Lambov, N, The effect of the water on the curcumin tautomerism: A quantitative approach, Spectrochimica Acta Part A: Molecular and Biomolecular Spectroscopy 132 (2014) 815-820.

* cited by examiner

*Primary Examiner* — Russell G Fiebig
(74) *Attorney, Agent, or Firm* — Jyoti C Iyer

(57) ABSTRACT

A composition for enhanced bioavailability of curcumin comprising a curcuminoid mixture and an essential oil of turmeric, wherein the curcuminoid mixture comprises a curcumin-keto compound, a curcumin-enol compound, a bisdemethoxycurcumin, a demethoxycurcumin, wherein a weight ratio of the curcumin-keto compound to the curcumin-enol compound ranges from about 0.12-0.20:0.8-0.88. A composition for enhanced lymphatic bioavailability of curcumin comprising a curcuminoid mixture and an essential oil of turmeric, wherein the curcuminoid mixture comprises a curcumin-keto compound, a curcumin-enol compound, a bisdemethoxycurcumin, a demethoxycurcumin, wherein a weight ratio of the curcumin-keto compound to the curcumin-enol compound ranges from about 0.12-0.20:0.8-0.88. Methods for making the composition for enhanced bioavailability of curcumin. Methods for making the composition for enhanced lymphatic bioavailability of curcumin.

26 Claims, 17 Drawing Sheets

SAMPLE 1

SAMPLE 2

SAMPLE 1

SAMPLE 2

SAMPLE 1

SAMPLE 2

SAMPLE 1

SAMPLE 2

CURCUMINOID COMPOSITION OF CURCUMIN-KETO, METHOD OF PREPARATION AND USE THEREOF

This Application is a by-pass continuation of international Application Ser. No PCT/IB2024/055537 filed Jun. 6, 2024, which claims priority to Indian complete Application Ser. No. 202441003735 filed May 16, 2024, which claims priority to Indian Provisional Appl. Ser. No. 202441003735 filed Jan. 18, 2024, all of which are incorporated in entirety by reference.

FIELD

A curcuminoid mixture having a curcumin-keto compound, a curcumin-enol compound, a bisdemethoxycurcumin, a demethoxycurcumin and wherein the curcuminoid mixture has a weight ratio of curcumin-keto compound to curcumin-enol compound ranging from about 0.12-0.20:0.8-0.88 by weight is disclosed. A composition for enhanced lymphatic bioavailability of curcumin having the curcuminoid mixture and essential oil of turmeric is disclosed.

BACKGROUND

In this section, we discuss several aspects of related work, including background and conventional technologies.

Curcumin, a naturally occurring polyphenolic compound found in turmeric, can exist in two main tautomeric forms: keto and enol. These tautomeric forms refer to different structural arrangements of the molecule resulting from the movement of hydrogen atoms and double bonds. The keto form is characterized by a carbonyl group (C=O), while the enol form features a hydroxyl group (—OH) adjacent to a double bond. In the natural product (*Curcuma longa* rhizomes) curcumin exists mainly in enol form. In the natural product, the ratio of curcumin-keto to curcumin-enol ranges from 0.04-0.10:0.90-0.95.

The antioxidant activity of curcumin is primarily attributed to its ability to donate hydrogen atoms or electrons to free radicals, thereby neutralizing their harmful effects. The keto form of curcumin is more likely to participate in these reactions due to its structure, which makes it a better hydrogen atom or electron donor. In the keto form of curcumin, there is an active methylene group (—CH2-) located between two electron-withdrawing carbonyl groups (C=O). This active methylene group is capable of donating a hydrogen atom (H-atom) to neutralize free radicals, which is a key mechanism of antioxidant activity. When curcumin donates an H-atom from the active methylene group, it forms a carbon radical which can be stabilized by resonance structures. This stabilization helps prevent the formation of more damaging free radicals and contributes to curcumin's antioxidant properties. The presence of the active methylene group as the reaction site is particularly significant in acidic or polar media. In polar and acidic mediums (such as acidic solutions), curcumin predominantly exists in its keto form. The keto form is more stable under these conditions and is the favored tautomeric form. In this form, curcumin is less prone to degradation.

In non-polar and basic mediums (such as alkaline solutions), curcumin can undergo degradation and is more likely to exist in its enol form. The enol form is less stable in basic environments and can undergo chemical reactions, including hydrolysis and degradation. This degradation process involves the breaking of the heptadienone moiety in curcumin, which results in the disappearance of the active methylene group (—CH2-) that is responsible for imparting antioxidant activity to curcumin. As a result, the degradation products, such as feruloylmethane and ferulic acid, do not possess the same antioxidant properties as curcumin. Therefore, in basic media, where curcumin undergoes this degradation pathway, its ability to act as an antioxidant is compromised, as it loses the structural features necessary for hydrogen atom donation to neutralize free radicals. In basic medium, curcumin undergoes autoxidation and can act as a pro-oxidant rather than an antioxidant.

It would be desirable to prepare curcumin formulations with improved stability and bioavailability.

SUMMARY

The disclosed teachings provide a composition for enhanced bioavailability of curcumin having a curcuminoid mixture and an essential oil of turmeric. The curcuminoid mixture includes a curcumin-keto compound, a curcumin-enol compound, a bisdemethoxycurcumin, a demethoxycurcumin. A weight ratio of the curcumin-keto compound to the curcumin-enol compound ranges from about 0.12-0.20:0.8-0.88.

The disclosed teachings provide a composition for enhanced bioavailability of curcumin, wherein the weight ratio for the curcumin-keto compound to the curcumin-enol compound is about 0.15: about 0.85.

The disclosed teachings provide a composition for enhanced bioavailability of curcumin, wherein the essential oil of turmeric comprises ar-turmerone. The disclosed teachings provide a composition for enhanced bioavailability of curcumin, wherein the essential oil of turmeric includes about 30% to about 60% ar-turmerone by weight of the essential oil of turmeric.

In the disclosed compositions for enhanced bioavailability of curcumin a weight ratio of the curcuminoid mixture to the essential of turmeric ranges from about 5:1 to about 20:1 by weight.

The disclosed teachings provide a free-flowing powder of the composition for enhanced bioavailability of curcumin.

The disclosed teachings provide a composition for enhanced bioavailability of curcumin having a surface area ranging from about 0.05 to about 0.3 $m^2/g$.

The disclosed teachings provide a composition for enhanced bioavailability of curcumin having a surface area of about 0.17 $m^2/g$.

The disclosed teachings provide a composition for enhanced bioavailability of curcumin having scanning electron microscopy (SEM) image as represented in any of FIG. 5B, FIG. 6B, FIG. 7B or FIG. 8B.

The disclosed teachings provide a composition for enhanced bioavailability of curcumin having a Fourier Transform Infrared Spectroscopy (FTIR) spectra as presented in FIG. 9B.

The disclosed teachings provide a composition for enhanced bioavailability of curcumin having a Nuclear Magnetic Resonance (NMR) spectra as presented in FIG. 10B.

The disclosed teachings provide a composition for enhanced bioavailability of curcumin of having a Matrix-Assisted Laser Desorption/Ionization Time-of-Flight (MALDI TOF) spectra as presented in FIG. 11B.

The disclosed teachings provide an oral dosage form having a composition for enhanced bioavailability of curcumin chosen from tablet, capsule, soft gel capsule, granule, powder, lozenge, syrup, elixir, solution or suspension.

The disclosed teachings provide a unit oral dosage form having the composition for enhanced bioavailability of curcumin chosen from tablet, capsule, soft gel capsule, granule, powder, lozenge, syrup, elixir, solution or suspension.

The disclosed teachings provide a composition for enhanced bioavailability of curcumin having a curcuminoid mixture and essential oil of turmeric prepared by a method, the method comprising:

suspending a curcuminoid mixture in about 10 to about 20 times water to form a suspension; refluxing the suspension at about 70° C. to about 95° C. for about 0.5 hour to about 5 hours to obtain a refluxed mixture;

evaporating water from the refluxed mixture under vacuum and at about 30° C. to about 60° C. till volume of the refluxed mixture is decreased to half to obtain an evaporated mixture;

adding an essential oil of turmeric to the evaporated mixture to form a blend;

drying the blend under vacuum at about 30° C. to about 65° C. to obtain the composition for enhanced bioavailability of curcumin.

The disclosed teachings provide a method of preparing the composition for enhanced bioavailability of curcumin comprising:

suspending a curcuminoid mixture in about 10 to about 20 times water to form a suspension;

refluxing the suspension at about 70° C. to about 95° C. for about 0.5 hour to about 5 hrs to obtain a refluxed mixture;

evaporating water from the refluxed mixture under vacuum and at about 30° C. to about 60° C. till volume of the refluxed mixture is decreased to half to obtain an evaporated mixture;

adding an essential oil of turmeric to the evaporated mixture to form a blend;

drying the blend under vacuum at about 30° C. to about 65° C. to obtain the composition for enhanced bioavailability of curcumin.

The disclosed teachings provide a method of treatment by administering the composition for enhanced bioavailability of curcumin.

The disclosed teachings provide a composition for enhanced lymphatic bioavailability of curcumin having a curcuminoid mixture and an essential oil of turmeric. The curcuminoid mixture includes a curcumin-keto compound, a curcumin-enol compound, a bisdemethoxycurcumin, and a demethoxycurcumin. A weight ratio of the curcumin-keto compound to the curcumin-enol compound ranges from about 0.12-0.20:0.8-0.88.

The disclosed teachings provide a composition for enhanced lymphatic bioavailability of curcumin, wherein the weight ratio of the curcumin-keto compound to the curcumin-enol compound is about 0.15:0.85.

The disclosed teachings provide a composition for enhanced lymphatic bioavailability of curcumin, wherein the essential oil of turmeric comprises ar-turmerone. A composition for enhanced lymphatic bioavailability of curcumin, wherein the essential oil of turmeric includes about 30% to about 60% ar-turmerone by weight of the essential oil of turmeric.

A composition for enhanced lymphatic bioavailability of curcumin, wherein a weight ratio of the curcuminoid mixture to the essential of turmeric ranges from about 5:1 to about 20:1 by weight.

A composition for enhanced lymphatic bioavailability of curcumin, wherein the composition is a free-flowing powder.

The disclosed teachings provide an oral dosage form having the composition for enhanced lymphatic bioavailability of curcumin chosen from tablet, capsule, soft gel capsule, granule, powder, lozenge, syrup, elixir, solution or suspension.

The disclosed teachings provide a unit oral dosage form having the composition for enhanced lymphatic bioavailability of curcumin chosen from tablet, capsule, soft gel capsule, granule, powder, lozenge, syrup, elixir, solution or suspension.

The disclosed teachings provide a composition for enhanced lymphatic bioavailability of curcumin, wherein the composition has a surface area ranging from about 0.05 to about 0.3 $m^2/g$.

The disclosed teachings provide a composition for enhanced lymphatic bioavailability of curcumin, wherein the composition comprises a surface area of about 0.17 $m^2/g$.

The disclosed teachings provide a composition for enhanced lymphatic bioavailability of curcumin of having a Scanning Electron Microscopy (SEM) image chosen from any of FIG. 5B, FIG. 6B, FIG. 7B or FIG. 8B.

The disclosed teachings provide a composition for enhanced lymphatic bioavailability of curcumin, having a Fourier Transform Infrared (FTIR) spectra as presented in FIG. 9B.

The disclosed teachings provide a composition for enhanced lymphatic bioavailability of curcumin of having a Nuclear Magnetic Resonance (NMR spectra) as presented in FIG. 10B.

The disclosed teachings provide a composition for enhanced bioavailability of curcumin having a Matrix-Assisted Laser Desorption/Ionization Time-of-Flight (MALDI TOF) spectra as presented in FIG. 11B.

The disclosed teachings provide a composition for enhanced lymphatic bioavailability of curcumin prepared by a method, the method comprising:

suspending a curcuminoid mixture in about 10 to about 20 times water to form a suspension;

refluxing the suspension at about 70° C. to about 95° C. for about 0.5 hour to about 5 hrs to obtain a refluxed mixture;

evaporating water from the refluxed mixture under vacuum and at about 30° C. to about 60° C. till volume of the refluxed mixture is decreased to half to obtain an evaporated mixture;

adding essential oil of turmeric to the evaporated mixture to form a blend;

drying the blend under vacuum at about 30° C. to about 65° C. to obtain the composition for enhanced lymphatic bioavailability of curcumin.

The disclosed teachings provide a method of preparing a composition for enhanced lymphatic bioavailability of curcumin, the method comprising:

suspending a curcuminoid mixture in about 10 to about 20 times water to form a suspension;

refluxing the suspension at about 70° C. to about 95° C. for about 0.5 hour to about 5 hrs to obtain a refluxed mixture;

evaporating water from the refluxed mixture under vacuum and at about 30° C. to about 60° C. till volume of the refluxed mixture is decreased to half to obtain an evaporated mixture;

adding essential oil of turmeric to the evaporated mixture to form a blend;

drying the blend under vacuum at about 30° C. to about 65° C. to obtain the composition for enhanced lymphatic bioavailability of curcumin.

The disclosed teachings provide a method of treatment comprising administering a composition for lymphatic bioavailability of curcumin.

Some embodiments disclose a composition for enhanced bioavailability of curcumin having a curcuminoid mixture and an essential oil, wherein the curcuminoid mixture comprises a curcumin-keto compound, a curcumin-enol compound, a bisdemethoxycurcumin, a demethoxycurcumin, wherein a weight ratio of the curcumin-keto compound to the curcumin-enol compound ranges from about 0.12-0.20: 0.8-0.88, and wherein the essential oil is chosen from essential oil of turmeric, essential oil of pepper, essential oil of ginger, essential oil of clove, essential oil of cinnamon, essential oil of boswellia, essential oil of nutmeg, essential oil of star anise, essential oil of lemon grass, essential oil of rosemary, essential oil of tea tree, essential oil of mustard oil, or essential oil of *ocimum*.

The disclosed teachings provide a method of preparing a composition for enhanced bioavailability of curcumin comprising a curcuminoid mixture and an essential oil, wherein the curcuminoid mixture comprises a curcumin-keto compound, a curcumin-enol compound, a bisdemethoxycurcumin, a demethoxycurcumin, wherein a weight ratio of the curcumin-keto compound to the curcumin-enol compound ranges from about 0.12-0.20:0.8-0.88, and wherein the essential oil is chosen from essential oil of turmeric, essential oil of pepper, essential oil of ginger, essential oil of clove, essential oil of cinnamon, essential oil of boswellia, essential oil of nutmeg, essential oil of star anise, essential oil of lemon grass, essential oil of rosemary, essential oil of tea tree, essential oil of mustard oil, or essential oil of *ocimum*, the method comprising:

suspending a curcuminoid mixture in about 10 to about 20 times water to form a suspension;

refluxing the suspension at about 70° C. to about 95° C. for about 0.5 hour to about 5 hrs to obtain a refluxed mixture;

evaporating water from the refluxed mixture under vacuum and at about 30° C. to about 60° C. till volume of the refluxed mixture is decreased to half to obtain an evaporated mixture;

adding the essential oil to the evaporated mixture to form a blend;

drying the blend under vacuum at about 30° C. to about 65° C. to obtain the composition for enhanced bioavailability of curcumin.

The disclosed teachings provide a composition for enhanced lymphatic bioavailability of curcumin comprising a curcuminoid mixture and an essential oil, wherein the curcuminoid mixture comprises a curcumin-keto compound, a curcumin-enol compound, a bisdemethoxycurcumin, a demethoxycurcumin, wherein a weight ratio of the curcumin-keto compound to the curcumin-enol compound ranges from about 0.12-0.20:0.8-0.88, and wherein the essential oil is chosen from essential oil of turmeric, essential oil of pepper, essential oil of ginger, essential oil of clove, essential oil of cinnamon, essential oil of boswellia, essential oil of nutmeg, essential oil of star anise, essential oil of lemon grass, essential oil of rosemary, essential oil of tea tree, essential oil of mustard oil, or essential oil of *ocimum*.

The disclosed teachings provide a method of preparing a composition for enhanced lymphatic bioavailability of curcumin comprising a curcuminoid mixture and an essential oil, wherein the curcuminoid mixture comprises a curcumin-keto compound, a curcumin-enol compound, a bisdemethoxycurcumin, a demethoxycurcumin, wherein a weight ratio of the curcumin-keto compound to the curcumin-enol compound ranges from about 0.12-0.20:0.8-0.88, and wherein the essential oil is chosen from essential oil of turmeric, essential oil of pepper, essential oil of ginger, essential oil of clove, essential oil of cinnamon, essential oil of boswellia, essential oil of nutmeg, essential oil of star anise, essential oil of lemon grass, essential oil of rosemary, essential oil of tea tree, essential oil of mustard oil, or essential oil of *ocimum*, the method comprising: suspending a curcuminoid mixture in about 10 to about 20 times water to form a suspension;

refluxing the suspension at about 70° C. to about 95° C. for about 0.5 hour to about 5 hrs to obtain a refluxed mixture;

evaporating water from the refluxed mixture under vacuum and at about 30° C. to about 60° C. till volume of the refluxed mixture is decreased to half to obtain an evaporated mixture;

adding the essential oil to the evaporated mixture to form a blend;

drying the blend under vacuum at about 30° C. to about 65° C. to obtain the composition for enhanced bioavailability of curcumin.

BRIEF DESCRIPTION OF THE DRAWINGS

The above objectives and advantages of the disclosed teachings will become more apparent by describing in detail preferred embodiments thereof with reference to the attached drawings in which.

DETAILED DESCRIPTION

Figure 1:
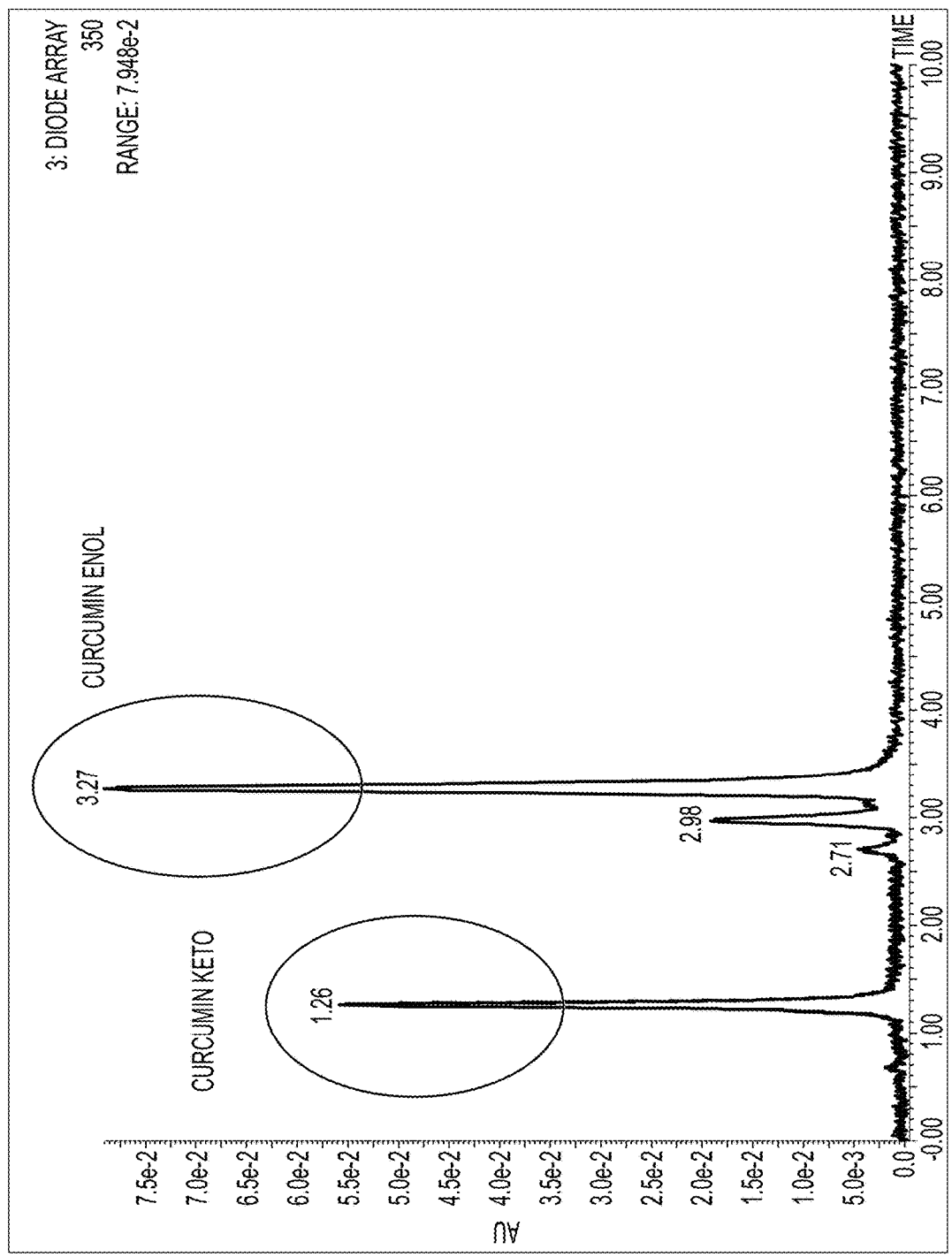
FIG. 1 represents high performance liquid chromatography (HPLC) chromatogram confirming the presence of keto and enol form of curcumin in regular turmeric extract (also referred to as "curcuminoid mixture alone").

Novel bioavailable curcumin formulations are disclosed herein having higher levels of curcumin-keto compound than found occurring in natural product (turmeric rhizomes). The disclosed bioavailable curcumin formulations are different as compared to other existing bioavailable curcumin formulations because the bioavailable curcumin formulations disclosed herein exhibit improved lymphatic bioavailability of curcumin. The bioavailable curcumin formulations disclosed herein also have improved stability because of higher levels of curcumin in keto form. The bioavailable curcumin formulations disclosed herein have a lesser surface area than the tested control formulations. Lesser surface area should have been correlated with lesser bioavailability of curcumin, however, unexpectedly the bioavailable curcumin formulations disclosed herein exhibited higher bioavailability of curcumin in blood and in lymph.

Disclosure provides curcuminoid mixtures having higher curcumin-keto compound prepared from *Curcuma longa* (turmeric)rhizomes. The disclosed curcuminoid mixtures include a curcumin-keto compound, a curcumin-enol compound, a bisdemethoxycurcumin, and a demethoxycurcumin, wherein a weight ratio of curcumin-keto compound to curcumin-enol compound ranges from about 0.12-0.20: 0.8-0.88, or about 0.13-0.19:0.81-0.87, or about 0.14-0.17: 0.82-0.86, or about 0.15-0.18:0.83-0.85, or about 0.16-0.19: 0.85-0.87, or about 0.15-0.18:0.84-0.88 by weight. The disclosed curcuminoid mixtures have greater amounts of curcumin-keto as compared to the natural product turmeric rhizomes. In some embodiments, the weight ratio of curcumin-keto compound to curcumin-enol compound is about 0.15:0.85, or about 0.14:0.86, or about 0.13:0.87, or about 0.12:0.88, or about 0.12:0.86.

Some embodiments disclose methods of preparing curcuminoid mixtures having more curcumin in keto form as compared to curcumin-keto compound found in turmeric rhizomes. A novel process of extracting turmeric rhizomes resulted in the disclosed curcuminoid mixtures having more curcumin in keto form than in enol forms compared to curcumin-keto found in naturally occurring turmeric rhizomes. A weight ratio of curcumin-keto to curcumin-enol in the disclosed curcuminoid mixtures and compositions ranges from about 0.12-0.20:0.8-0.88 by weight. In the curcuminoid mixtures prepared by the novel extraction process which includes a refluxing step, the keto form of curcumin is increased by 40-50% and enol form is reduced by 15-25% as compared to turmeric rhizomes.

In some embodiments, the disclosure provides bioavailable curcumin compositions for enhancing bioavailability of curcumin in blood, wherein the bioavailability of curcumin is enhanced by blending curcuminoid mixtures disclosed herein and an essential oil, wherein the curcuminoid mixture has a curcumin-keto compound, a curcumin-enol compound, a bisdemethoxycurcumin, a demethoxycurcumin, and wherein the essential oil can be chosen from essential oil of turmeric, essential oil of pepper, essential oil of ginger, essential oil of clove, essential oil of cinnamon, essential oil of boswellia, essential oil of nutmeg, essential oil of star anise, essential oil of lemon grass, essential oil of rosemary, essential oil of tea tree, essential oil of mustard oil, or essential oil of *ocimum*, and wherein the weight ratio of curcumin-keto compound to curcumin-enol compound in the bioavailable curcumin formulations ranges from about 0.12-0.20:0.8-0.88, or about 0.13-0.19:0.81-0.87, or about 0.14-0.17:0.82-0.86, or about 0.15-0.18:0.83-0.85, or about 0.16-0.19:0.85-0.87, or about 0.15-0.18:0.84-0.88 by weight. In some embodiments, the weight ratio of curcumin-keto compound to curcumin-enol compound is about 0.15: 0.85, or about 0.14:0.86, or about 0.13:0.87, or about 0.12:0.88, or about 0.12:0.86.

In some embodiments, the disclosure provides bioavailable curcumin compositions for enhancing bioavailability of curcumin in lymph, wherein the bioavailability of curcumin is enhanced by blending curcuminoid mixtures disclosed herein and an essential oil, wherein the curcuminoid mixture has a curcumin-keto compound, a curcumin-enol compound, a bisdemethoxycurcumin, a demethoxycurcumin, and wherein the essential oil can be chosen from essential oil of turmeric, essential oil of pepper, essential oil of ginger, essential oil of clove, essential oil of cinnamon, essential oil of boswellia, essential oil of nutmeg, essential oil of star anise, essential oil of lemon grass, essential oil of rosemary, essential oil of tea tree, essential oil of mustard oil, or essential oil of *ocimum*, and wherein the weight ratio of curcumin-keto compound to curcumin-enol compound in the bioavailable curcumin formulations ranges from about 0.12-0.20:0.8-0.88, or about 0.13-0.19:0.81-0.87, or about 0.14-0.17:0.82-0.86, or about 0.15-0.18:0.83-0.85, or about 0.16-0.19:0.85-0.87, or about 0.15-0.18:0.84-0.88 by weight. In some embodiments, the weight ratio of curcumin-keto compound to curcumin-enol compound is about 0.15: 0.85, or about 0.14:0.86, or about 0.13:0.87, or about 0.12:0.88, or about 0.12:0.86.

The disclosed teachings provide a composition for enhanced bioavailability of curcumin having a curcuminoid mixture and an essential oil of turmeric. The curcuminoid mixture includes a curcumin-keto compound, a curcumin-enol compound, a bisdemethoxycurcumin, a demethoxycurcumin. A weight ratio of the curcumin-keto compound to the curcumin-enol compound ranges from about 0.12-0.20:0.8-0.88. Some embodiments provide a composition for enhanced bioavailability of curcumin, wherein the weight ratio for the curcumin-keto compound to the curcumin-enol compound is about 0.15: about 0.85. In the disclosed compositions for enhanced bioavailability of curcumin, the essential oil of turmeric comprises ar-turmerone. In some embodiments for the composition for enhanced bioavailability of curcumin, the essential oil of turmeric includes about 30% to about 60% ar-turmerone by weight of the essential oil of turmeric. In the disclosed compositions for enhanced bioavailability of curcumin a weight ratio of the curcuminoid mixture to the essential of turmeric ranges from about 5:1 to about 20:1 by weight. A free-flowing powder of the composition for enhanced bioavailability of curcumin. Some embodiments of the composition for enhanced bioavailability of curcumin have a surface area ranging from about 0.05 to about 0.3 m$^2$/g. Some embodiments of the composition for enhanced bioavailability of curcumin have a surface area of about 0.17 m$^2$/g. Some embodiments of the composition for enhanced bioavailability of curcumin have scanning electron microscopy (SEM) image as represented in any of FIG. 5B, FIG. 6B, FIG. 7B or FIG. 8B. Some embodiments of the disclosed composition for enhanced bioavailability of curcumin have a Fourier Transform Infrared Spectroscopy (FTIR) spectra as presented in FIG. 9B. Some embodiments of the disclosed composition for enhanced bioavailability of curcumin have a Nuclear Magnetic Resonance (NMR) spectra as presented in FIG. 10B. Some embodiments of the composition for enhanced bioavailability of curcumin of have a Matrix-Assisted Laser Desorption/Ionization Time-of-Flight (MALDI TOF) spectra as presented in FIG. 11B. Some embodiments provide an oral dosage form having a composition for enhanced bioavailability of curcumin such as a tablet, capsule, soft gel capsule, granule, powder, lozenge, syrup, elixir, solution or suspension. Some embodiments provide a unit oral dosage form having the disclosed compositions for enhanced bioavailability of curcumin such as a tablet, capsule, soft gel capsule, granule, powder, lozenge, syrup, elixir, solution or suspension.

The disclosed teachings provide a composition for enhanced lymphatic bioavailability of curcumin having a curcuminoid mixture and an essential oil of turmeric. The curcuminoid mixture includes a curcumin-keto compound, a curcumin-enol compound, a bisdemethoxycurcumin, a demethoxycurcumin. A weight ratio of the curcumin-keto compound to the curcumin-enol compound ranges from about 0.12-0.20:0.8-0.88. Some embodiments provide a composition for enhanced lymphatic bioavailability of curcumin, wherein the weight ratio for the curcumin-keto compound to the curcumin-enol compound is about 0.15: about 0.85. In the disclosed compositions for enhanced lymphatic bioavailability of curcumin, the essential oil of turmeric comprises ar-turmerone. In some embodiments for the composition for enhanced lymphatic bioavailability of curcumin, the essential oil of turmeric includes about 30% to about 60% ar-turmerone by weight of the essential oil of turmeric. In the disclosed compositions for enhanced lymphatic bioavailability of curcumin a weight ratio of the curcuminoid mixture to the essential of turmeric ranges from about 5:1 to about 20:1 by weight. A free-flowing powder of the composition for enhanced lymphatic bioavailability of curcumin. Some embodiments of the composition for enhanced lymphatic bioavailability of curcumin have a surface area ranging from about 0.05 to about 0.3 m$^2$/g. Some embodiments of the composition for enhanced lymphatic bioavailability of curcumin have a surface area of about 0.17 m$^2$/g. Some embodiments of the composition for enhanced lymphatic bioavailability of curcumin have scanning electron microscopy (SEM) image as represented in any of FIG. 5B, FIG. 6B, FIG. 7B or FIG. 8B. Some embodiments of the disclosed composition for enhanced lymphatic bioavailability of curcumin have a Fourier Transform Infrared Spectroscopy (FTIR) spectra as presented in FIG. 9B. Some embodiments of the disclosed composition for enhanced lymphatic bioavailability of curcumin have a Nuclear Magnetic Resonance (NMR) spectra as presented in FIG. 10B. Some embodiments of the composition for enhanced lymphatic bioavailability of curcumin of have a Matrix-Assisted Laser Desorption/Ionization Time-of-Flight (MALDI TOF) spectra as presented in FIG. 11B. Some embodiments provide an oral dosage form having a composition for enhanced lymphatic bioavailability of curcumin such as a tablet, capsule, soft gel capsule, granule, powder, lozenge, syrup, elixir, solution or suspension. Some embodiments provide a unit oral dosage form having the disclosed compositions for enhanced lymphatic bioavailability of curcumin such as a tablet, capsule, soft gel capsule, granule, powder, lozenge, syrup, elixir, solution or suspension.

Bioavailable curcumin formulations are disclosed herein for enhanced bioavailability of curcumin in blood and/or in lymphatic tissues having a curcuminoid mixture and an essential oil of turmeric, wherein the curcuminoid mixture has a curcumin-keto compound, a curcumin-enol compound, a bisdemethoxycurcumin, a demethoxycurcumin, and wherein a weight ratio of curcumin-keto compound to curcumin-enol compound in the bioavailable curcumin formulations ranges from about 0.12-0.20:0.8-0.88. Some embodiments of the bioavailable curcumin formulations disclosed herein provide a composition for enhanced bioavailability of curcumin. Some embodiments of the bioavailable curcumin formulations disclosed herein provide a composition for enhanced lymphatic bioavailability of curcumin. The disclosed bioavailable curcumin formulations are prepared by a novel extraction method requiring refluxing of curcuminoid mixture which results in a 40-50% increase in curcumin-keto form and 15-25% decrease in curcumin-enol form in the bioavailable curcumin formulation as compared to a control physical blend of curcuminoid mixture and essential oil of turmeric. In the control physical blend, the curcuminoid mixture is not refluxed prior to blending with essential oil of turmeric. The bioavailable curcumin formulations disclosed herein having enhanced bioavailability of curcumin is a free flowing, non-sticky powder composition with no leaching out of oil from the bioavailable curcumin formulations.

The disclosure provides bioavailable curcumin formulations for enhanced bioavailability of curcumin in blood and/or in lymphatic tissues having a curcuminoid mixture and an essential oil of turmeric. Curcuminoid mixture includes a curcumin-keto compound, a curcumin-enol compound, a bisdemethoxycurcumin, and a demethoxycurcumin, and wherein the weight ratio of curcumin-keto compound to curcumin-enol compound in the bioavailable curcumin formulations ranges from about 0.12-0.20:0.8-0.88, or about 0.13-0.19:0.81-0.87, or about 0.14-0.17:0.82-0.86, or about 0.15-0.18:0.83-0.85, or about 0.16-0.19:0.85-0.87, or about 0.15-0.18:0.84-0.88 by weight. In some embodiments, the weight ratio of curcumin-keto compound to curcumin-enol compound is about 0.15:0.85, or about 0.14:0.86, or about 0.13:0.87, or about 0.12:0.88, or about 0.12:0.86.

Some disclosed bioavailable curcumin formulations for enhanced bioavailability of curcumin in blood and/or in lymph have a uniform blend of curcuminoid mixture (with higher curcumin-keto compound) and essential oil of turmeric having ar-turmerone (aromatic turmerone). Essential oil of turmeric having ar-turmerone are prepared by generally known methods of fractionation such as steam distillation or hydrodistillation etc. In some embodiments, essential oil of turmeric includes about 30% to about 60%, about 35% to about 55%, about 40% to about 50%, about 30%, about 35%, about 38%, about 39%, about 40%, about 41%, about 42%, about 43%, about 44%, about 45%, about 46%, about 47%, about 48%, about 49%, about 50%, about 52%, about 54%, about 56%, about 58%, or about 60% ar-turmerone by weight of the essential oil of turmeric.

In some bioavailable curcumin formulations for enhanced bioavailability of curcumin in blood and/or in lymph, a weight ratio of the curcuminoid mixture (having higher curcumin-keto compound) to the essential oil of turmeric ranges from about 5:1 to about 20:1, or about 6:1 to about 12:1, or about 8:1 to about 15:1, or about 10:1 to about 18:1, or about 13:1 to about 16:1, or about 5:1, about 6:1, about 7:1, about 8:1, about 9:1, about 10:1, about 11:1, about 12:1, about 13:1, about 14:1, about, about 15:1, about 16:1, about 17:1, about 18:1, about 19:1, about 20:1.

Disclosed compositions for enhanced bioavailability of curcumin in blood or enhanced bioavailability of curcumin in lymph have a surface area ranging from about 0.05 to about 0.3 $m^2/g$, or about 0.06 to about 0.29 $m^2/g$, or about 0.07 to about 0.28 $m^2/g$, or about 0.08 to about 0.27 $m^2/g$, or about 0.09 to about 0.26 $m^2/g$, or about 0.09 to about 0.25 $m^2/g$, or about 0.10 to about 0.24 $m^2/g$, or about 0.11 to about 0.23 $m^2/g$, or about 0.12 to about 0.22 $m^2/g$, or about 0.13 to about 0.21 $m^2/g$, or about 0.14 to about 0.20 $m^2/g$, or about 0.15 to about 0.19 $m^2/g$, or about 0.16 to about 0.18 $m^2/g$, or about 0.17 to about 0.18 $m^2/g$, or about 0.05 $m^2/g$, or about 0.07 $m^2/g$, or about 0.09 $m^2/g$, or about 0.11 $m^2/g$, or about 0.13 $m^2/g$, or about 0.15 $m^2/g$, or about 0.17 $m^2/g$, or about 0.19 $m^2/g$, or about 0.21 $m^2/g$, or about 0.23 $m^2/g$, or about 0.25 $m^2/g$, or about 0.27 $m^2/g$, or about 0.29 $m^2/g$, or about 0.3 $m^2/g$.

The disclosure provides a method of extraction of a curcuminoid mixture having more of curcumin in a keto form. In the method, curcuminoids are extracted from turmeric rhizomes by solvent extraction. Suitable solvents for this purpose include acetone, hexane, ethyl acetate, dicholoroethane, chloroform, etc. Extracted curcuminoid mixture is suspended in water to form a suspension. The suspension is refluxed with water at a temperature ranging from about 70° C. to about 95° C. for about 0.5 hours to about 5 hrs, or about 80° C. to about 90° C. for about 2 hours to about 4 hrs, or about 85° C. to about 95° C. for 3-4 hrs, or about 75° C. to about 85° C. for about 1 hour to about 3 hrs, or about 95° C. for about 4 hrs. Water is evaporated at under vacuum at about 30° C. to about 60° C. to obtain an evaporated refluxed curcuminoid mixture that has increased concentration of curcumin in a keto form as compared to curcuminoid mixture prepared from turmeric rhizomes without a step of refluxing the curcuminoid mixture extracted from turmeric rhizomes with water at about 70° C. to about 95° C. for about 0.5 to about 5 hrs.

The disclosure provides a method of preparation of bioavailable curcumin formulations with enhanced bioavailability of curcumin in blood and/or in lymph having a curcuminoid mixture and an essential oil of turmeric, wherein the curcuminoid mixture has more of curcumin in a keto form as compared to the curcumin-keto in naturally occurring turmeric rhizomes. In the method of extracting curcuminoid mixture, curcuminoids are extracted by solvent extraction. Suitable solvents for this purpose include acetone, hexane, ethyl acetate, dicholoroethane, chloroform, etc. Extracted curcuminoid mixture is suspended in water to form a suspension. Suspension is heterogeneous mixture in which solid particles are dispersed in a liquid medium but are not dissolved. In a suspension, the solid particles might settle out over time if the suspension is left undisturbed. The suspension of curcuminoids in water was refluxed at about 70° C. to about 95° C. for about 0.5 to about 5 hrs. Refluxing involves the continuous boiling of a liquid and condensing the vapors back into the original vessel. Water is evaporated from the refluxed curcuminoid mixture at under vacuum at about 30-60° C. until the volume of the total refluxed curcuminoid mixture is reduced to half. Essential oil or volatile oils are isolated by steam distillation. Essential oil of turmeric is added to the refluxed curcuminoid mixture in a range ratio of about 5:1 to about 20:1 of curcuminoid mixture to essential oil of turmeric and blended. The final blended bioavailable curcumin formulation is a free flowing, non-sticky powder. Oil does not leach out from the blended composition. In some embodiments, the curcumin-keto:curcumin-enol ratio in the bioavailable curcumin formulation is about 0.15:0.85. There is a 40-50% increase in curcumin-keto form and 15-25% decrease in curcumin-enol form in the bioavailable curcumin formulations as compared to control physical blend (prepared without refluxing the curcuminoid mixture prior to adding the essential oil of turmeric).

Some embodiments provide a method of preparing a composition for enhanced bioavailability of curcumin having a curcuminoid mixture and essential oil of turmeric, the method comprising:
 suspending a curcuminoid mixture in about 10 to about 20 times water to form a suspension;
 refluxing the suspension at about 70° C. to about 95° C. for about 0.5 hour to about 5 hrs to obtain a refluxed mixture;
 evaporating water from the refluxed mixture under vacuum and at about 30° C. to about 60° C. till volume of the refluxed mixture is decreased to half to obtain an evaporated mixture;
 adding an essential oil of turmeric to the evaporated mixture to form a blend;
 drying the blend under vacuum at about 30° C. to about 65° C. to obtain the composition for enhanced bioavailability of curcumin.

Some embodiments provide a method of preparing a composition for enhanced lymphatic bioavailability of curcumin having a curcuminoid mixture and essential oil of turmeric, the method comprising:
 suspending a curcuminoid mixture in about 10 to about 20 times water to form a suspension;
 refluxing the suspension at about 70° C. to about 95° C. for about 0.5 hour to about 5 hrs to obtain a refluxed mixture;
 evaporating water from the refluxed mixture under vacuum and at about 30° C. to about 60° C. till volume of the refluxed mixture is decreased to half to obtain an evaporated mixture;
 adding an essential oil of turmeric to the evaporated mixture to form a blend; drying the blend under vacuum at about 30° C. to about 65° C. to obtain the composition for enhanced lymphatic bioavailability of curcumin.

Some embodiments provide a method of preparing a composition for enhanced bioavailability of curcumin having a curcuminoid mixture and an essential oil, wherein the curcuminoid mixture comprises a curcumin-keto compound, a curcumin-enol compound, a bisdemethoxycurcumin, a demethoxycurcumin, wherein a weight ratio of the curcumin-keto compound to the curcumin-enol compound ranges from about 0.12-0.20:0.8-0.88, and wherein the essential oil is chosen from essential oil of turmeric, essential oil of pepper, essential oil of ginger, essential oil of clove, essential oil of cinnamon, essential oil of boswellia, essential oil of nutmeg, essential oil of star anise, essential oil of lemon grass, essential oil of rosemary, essential oil of tea tree, essential oil of mustard oil, or essential oil of *ocimum*, the method comprising:

suspending a curcuminoid mixture in about 10 to about 20 times water to form a suspension;

refluxing the suspension at about 70° C. to about 95° C. for about 0.5 hour to about 5 hrs to obtain a refluxed mixture;

evaporating water from the refluxed mixture under vacuum and at about 30° C. to about 60° C. till volume of the refluxed mixture is decreased to half to obtain an evaporated mixture;

adding the essential oil to the evaporated mixture to form a blend;

drying the blend under vacuum at about 30° C. to about 65° C. to obtain the composition for enhanced bioavailability of curcumin.

Some embodiments provide a method of preparing a composition for enhanced lymphatic bioavailability of curcumin having a curcuminoid mixture and an essential oil, wherein the curcuminoid mixture comprises a curcumin-keto compound, a curcumin-enol compound, a bisdemethoxycurcumin, a demethoxycurcumin, wherein a weight ratio of the curcumin-keto compound to the curcumin-enol compound ranges from about 0.12-0.20:0.8-0.88, and wherein the essential oil is chosen from essential oil of turmeric, essential oil of pepper, essential oil of ginger, essential oil of clove, essential oil of cinnamon, essential oil of boswellia, essential oil of nutmeg, essential oil of star anise, essential oil of lemon grass, essential oil of rosemary, essential oil of tea tree, essential oil of mustard oil, or essential oil of *ocimum*, the method comprising: suspending a curcuminoid mixture in about 10 to about 20 times water to form a suspension;

refluxing the suspension at about 70° C. to about 95° C. for about 0.5 hour to about 5 hrs to obtain a refluxed mixture;

evaporating water from the refluxed mixture under vacuum and at about 30° C. to about 60° C. till volume of the refluxed mixture is decreased to half to obtain an evaporated mixture;

adding the essential oil to the evaporated mixture to form a blend;

drying the blend under vacuum at about 30° C. to about 65° C. to obtain the composition for enhanced lymphatic bioavailability of curcumin.

From the morphological and topological analysis of the disclosed bioavailable curcumin formulations (prepared by refluxing curcuminoid mixture prior to blending with essential oil of turmeric, a definite pattern and more crystalline nature was observed as compared to regular turmeric extract (curcuminoid mixture alone) or a control physical blend of curcuminoid mixture (without refluxing) and essential oil of turmeric.

Scanning electron microscopy (SEM) is an imaging technique used to examine the surface morphology and composition of samples at high resolution. SEM provides information about the topography, size, shape, and distribution of particles or features on a sample surface. SEM analysis shows that surface area of bioavailable curcumin formulation (Sample 2; FIGS. 5B, 6B, 7B and 8B) is lower as compared to the control physical blend of curcuminoids and essential oil of turmeric (Sample 1; FIGS. 5A, 6A, 7A and 8A).

Brunauer-Emmett-Teller (BET) surface area analysis is a widely used method to determine the specific surface area of solid materials, particularly porous materials such as powders, catalysts, and adsorbents. The BET method is based on the adsorption of gas molecules onto the surface of a solid material. The principle underlying the technique is the formation of a monolayer of adsorbed gas molecules on the material's surface. The BET equation relates the amount of adsorbed gas to the pressure of the gas and is based on the assumption of multilayer adsorption. BET analysis (Example 9) showed that bioavailable curcumin formulations (Sample 2) exhibited lower surface area (0.17787 $m^2/g$; Table 3) as compared to control physical blend (Sample 1, 0.8429 $m^2/g$; Table 3). However, unexpectedly the bioavailable curcumin formulations exhibited higher activity (in terms of bioavailability of curcumin) as compared to control physical blend which had a greater surface area. The reduced surface area observed in Sample 2 might be attributed to the entrapment of essential oil within the pores of the bioavailable curcumin formulation, whereby oil leaching from bioavailable curcumin formulation is decreased.

The disclosed bioavailable curcumin formulations are free-flowing powders. A free-flowing powder is a dry, granular substance that flows freely and easily when poured or dispensed. It does not clump together or form aggregates, allowing it to move smoothly and uniformly. The free-flowing powder has low cohesion: Particles in the powder have minimal attraction to each other, preventing clumping or sticking together. The free-flowing powder has good flowability: The powder flows readily when poured or dispensed without requiring excessive force or shaking. The free-flowing powder has uniform particle size: Consistent particle size distribution contributes to better flow properties and prevents segregation. The free-flowing powder has low moisture content: Moisture can lead to agglomeration and poor flowability, so free-flowing powders have low moisture content.

Figure 9A:
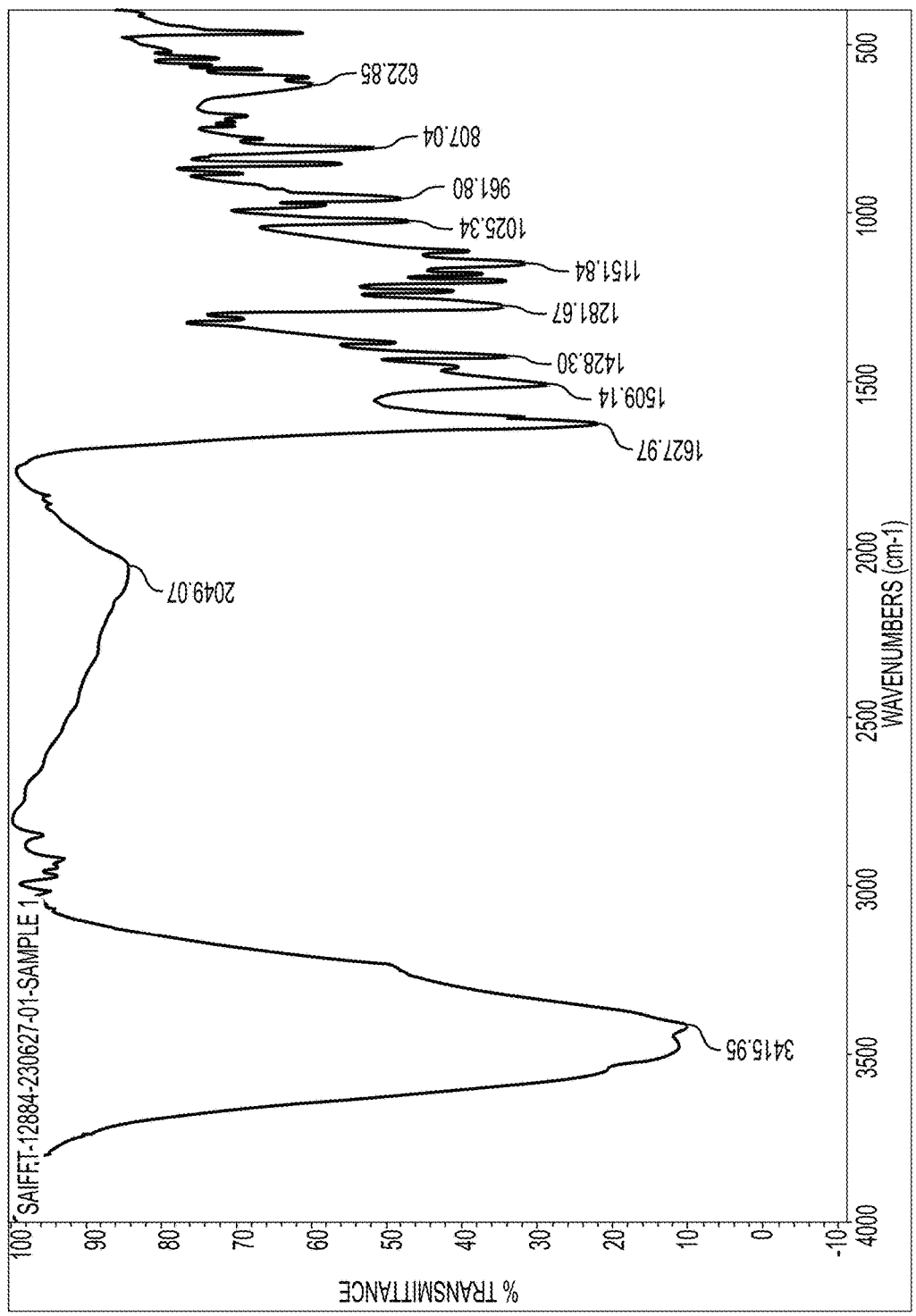
FIG. 9A represents Fourier Transform Infrared Spectroscopy (FTIR) spectra of Sample 1 (Control physical blend).

FTIR is widely used for qualitative and quantitative analysis of organic and inorganic compounds and is valuable for identifying unknown substances, studying polymer properties, and analyzing the composition of complex mixtures. FTIR pattern of control physical blend (Sample 1) in comparison with bioavailable curcumin formulation (Sample 2) is represented in FIGS. 9A (Sample 1) and 9B (Sample 2). The result shows that there is a difference in the position of certain absorption peaks between Sample 1 and Sample 2. These differences indicate interaction between the molecules or changes in the environment surrounding functional group in Sample 2. FTIR spectroscopy measures the absorption or emission of infrared radiation by a sample.

Figure 10A:
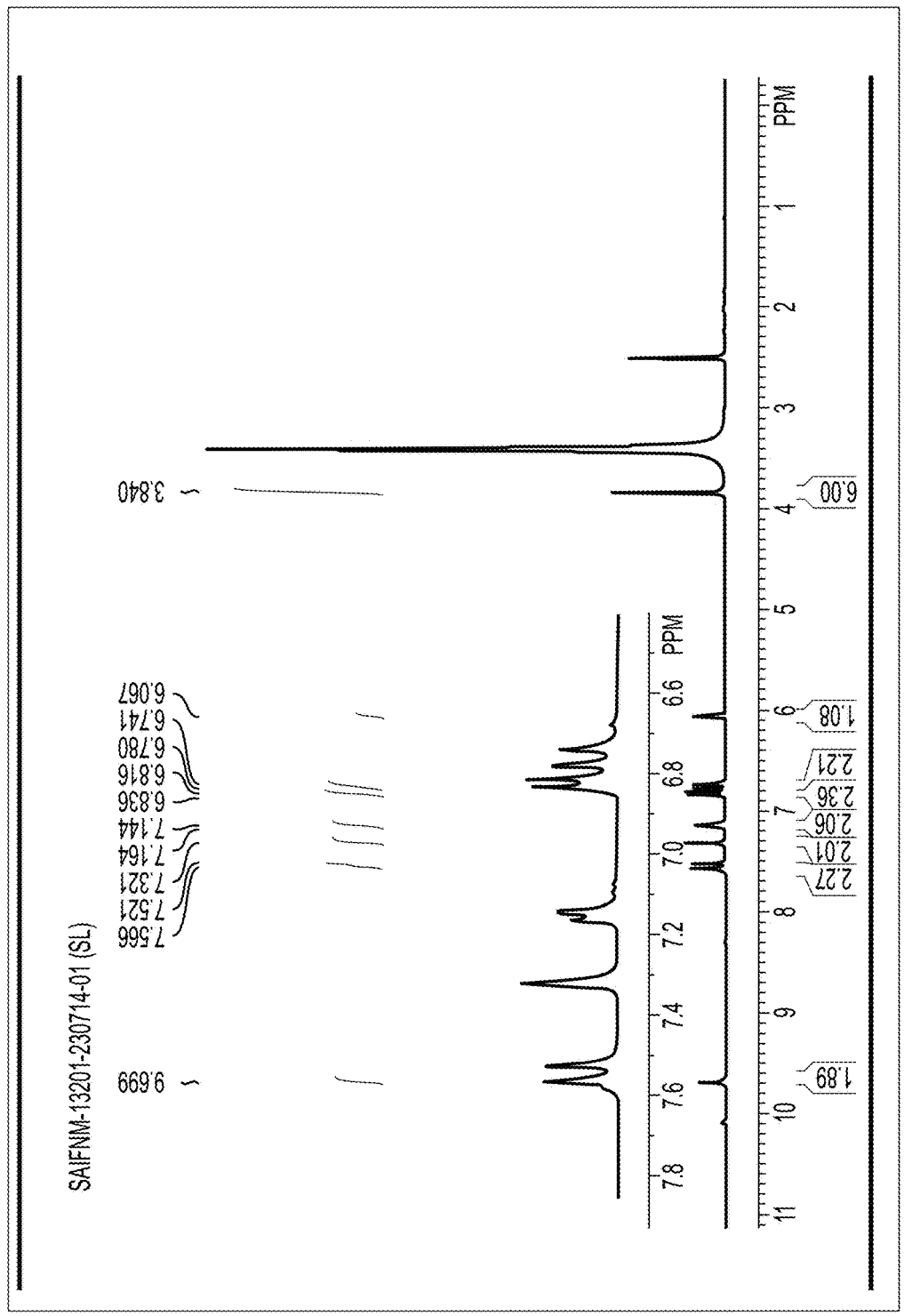
FIG. 10A represents Nuclear Magnetic Resonance (NMR) spectra of Sample 1 (Control physical blend).
Figure 10B:
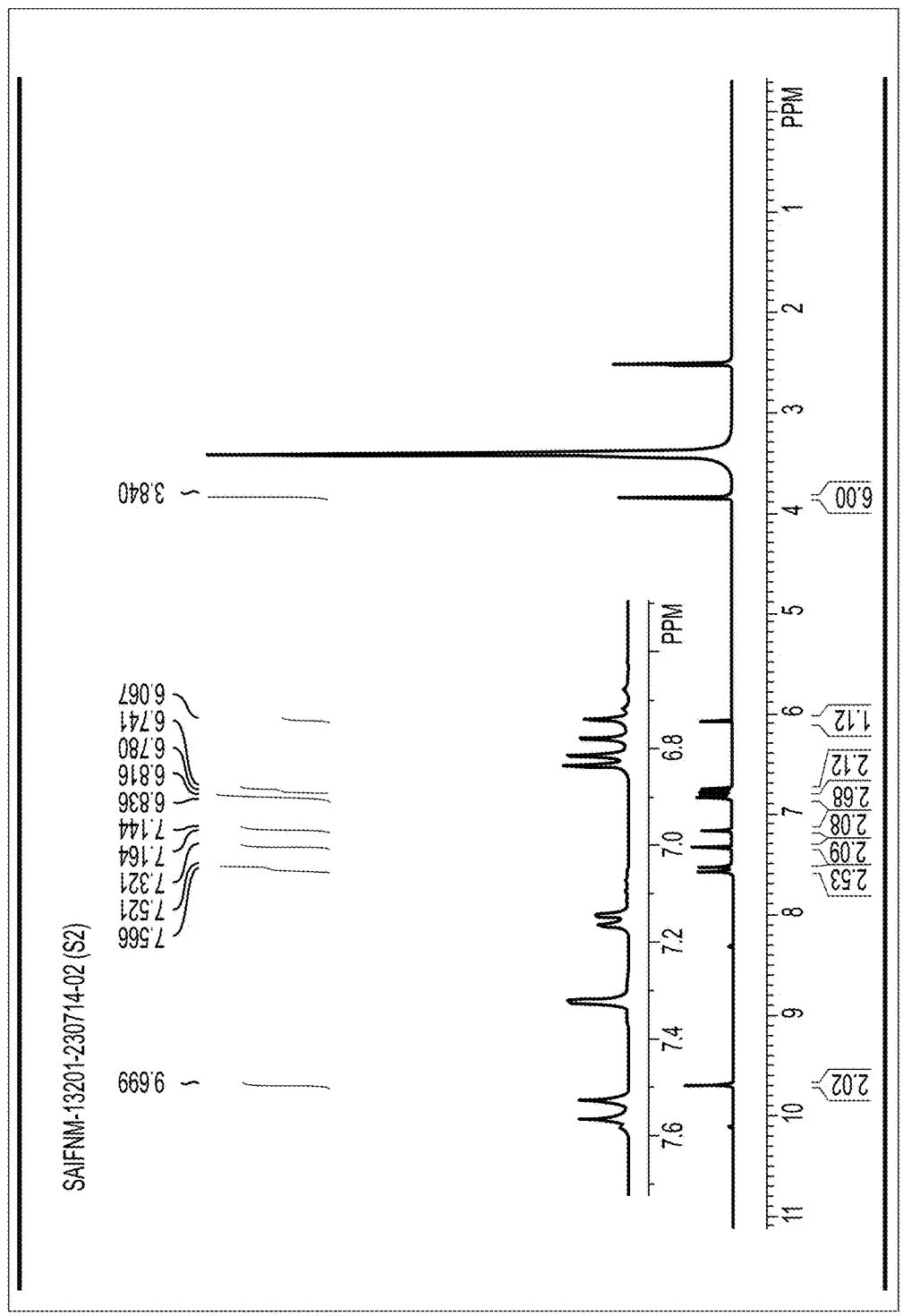
FIG. 10B represents NMR Spectra of Sample 2 (Bioavailable curcumin formulation).

NMR spectroscopy is a technique used to determine the physical and chemical properties of atoms or molecules by studying their nuclear magnetic moments. NMR provides information about the molecular structure, dynamics, and interactions in a sample and is helpful for characterizing biomolecules. NMR pattern of control physical blend (Sample 1) in comparison with bioavailable curcumin formulation (Sample 2) is represented in FIGS. 10A (Sample 1) and 10B (Sample 2). In Sample 2 compared to Sample 1, there is change in chemical shift which are indicative of the electronic environment of specific nuclei in the molecule. In Sample 2 changes in the chemical shifts or splitting patterns compared to the spectrum of Sample 1 may indicate interactions between curcuminoids and components of the essential oil prepared under refluxing condition. These interactions could result in shielding or deshielding effects on certain protons, leading to shifts in their resonance frequencies.

Figure 11A:
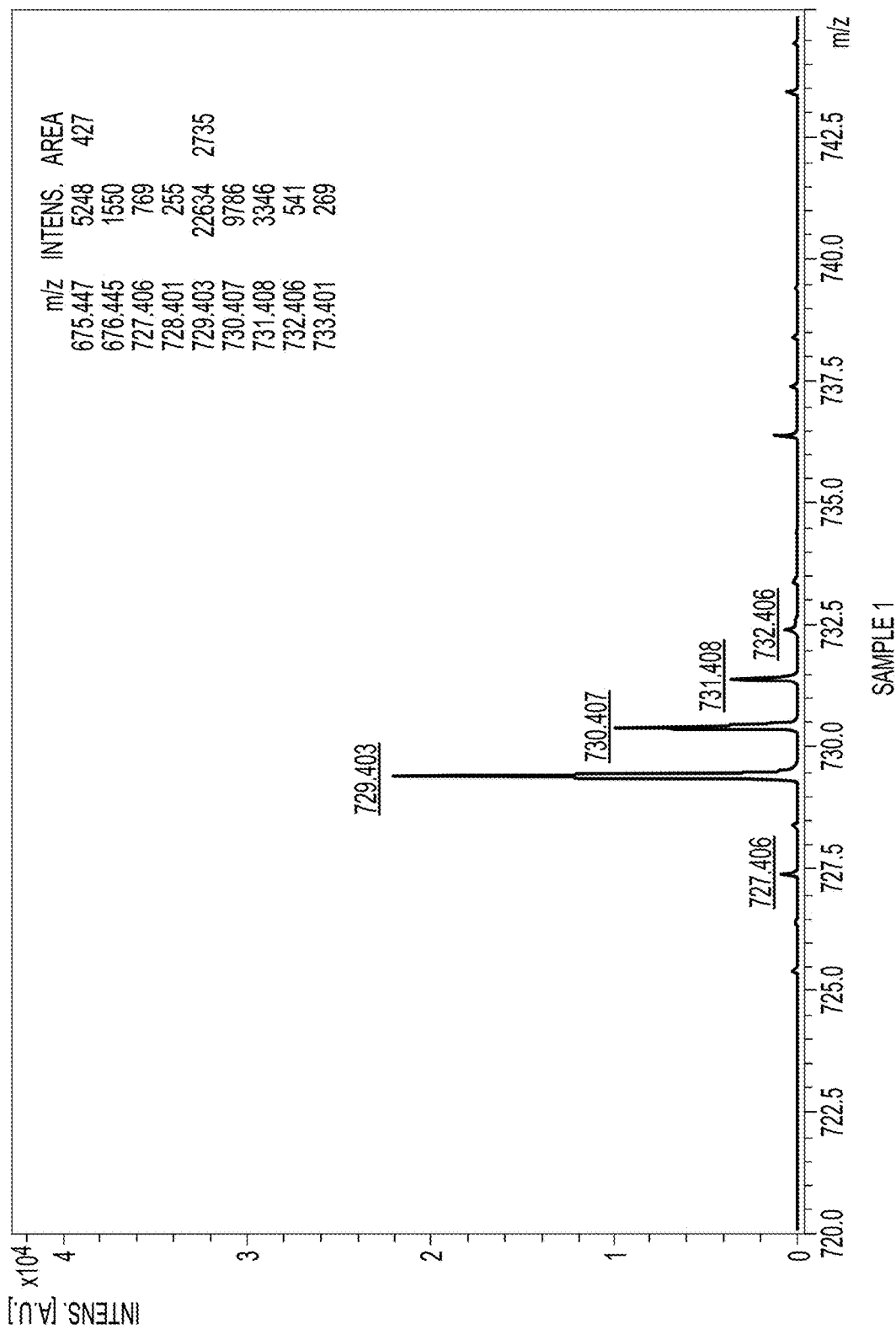
FIG. 11A represents Matrix-Assisted Laser Desorption/Ionization Time-of-Flight (MALDI TOF) spectra of Sample 1 (Control physical blend).
Figure 11B:
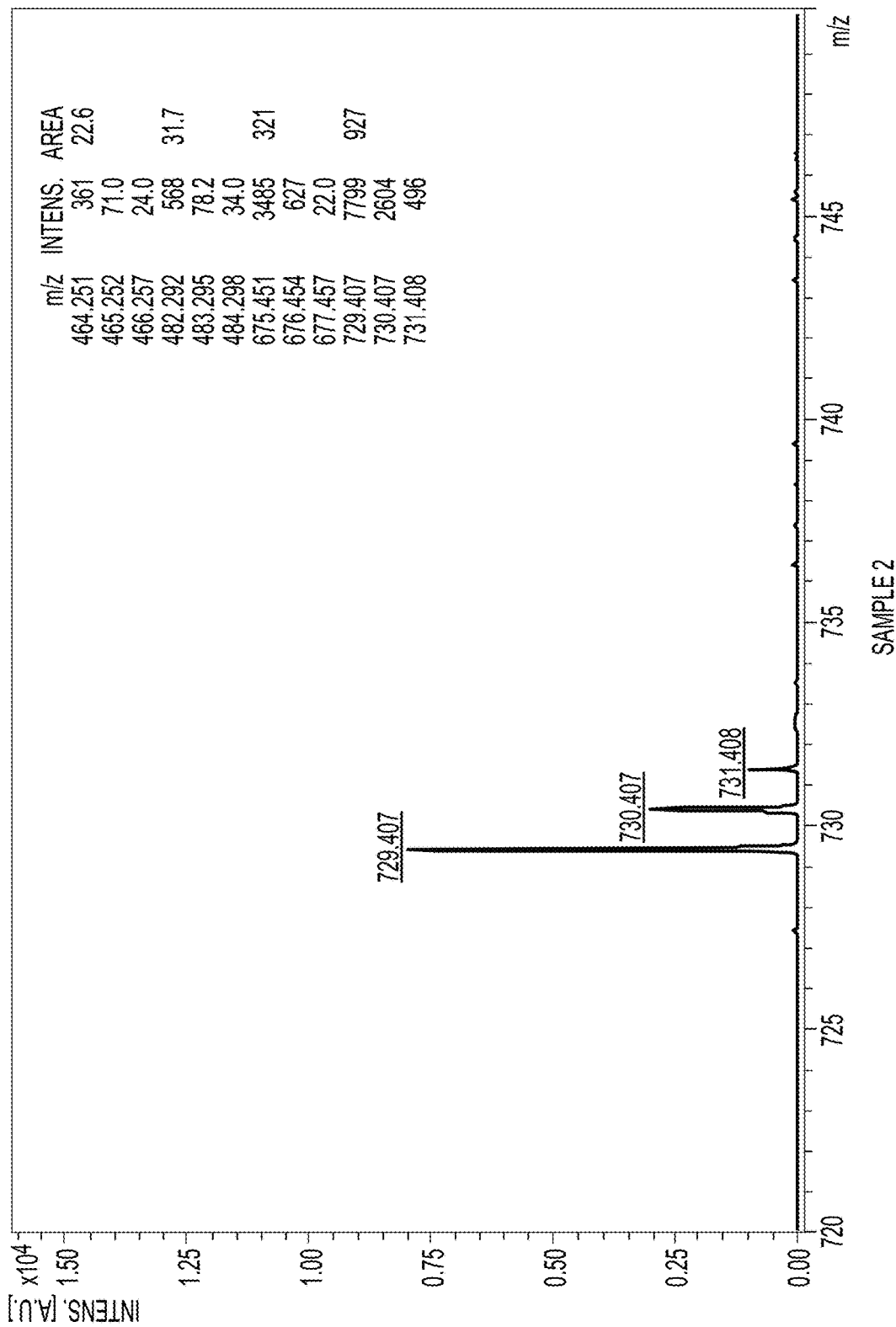
FIG. 11B represents MALDI TOF spectra of Sample 2 (Bioavailable curcumin formulation).

MALDI-TOF MS is a mass spectrometry technique used for the analysis of biomolecules. MALDI-TOF MS provides mass measurements of biomolecules, allowing for the identification, quantification, and structural analysis of biomolecules. MALDI-TOF pattern of control physical blend (Sample 1) in comparison with bioavailable curcumin formulation (Sample 2) is represented in FIG. 11A (Sample 1) and FIG. 11B (Sample 2). Y-axis in FIGS. 11A and 11B shows intensity (INTENS.) in absorbance units (A.U.) In Sample 2, there is a slight shift in m/z values compared to Sample 1. These shifts indicate interactions between curcuminoids and components of the essential oil prepared under refluxing condition.

In some embodiments of the bioavailable curcumin formulation, the blending ratio of curcuminoid mixture (with the curcuminoids extracted by refluxing) and essential oil of turmeric ranges from about 5:1 to about 20:1. In some embodiments of the bioavailable curcumin formulations, the blending ratio of curcuminoid mixture (with the curcuminoids extracted by refluxing) and essential oil of turmeric is about 10:1, about 12:1, or about 15:1. In these embodiments, the curcuminoid mixture includes a curcumin-keto compound, a curcumin-enol compound, a bisdemethoxycurcumin, and a demethoxycurcumin, and a ratio of the curcumin-keto to curcumin-enol ranges from about 0.12-0.20: 0.8-0.88 by weight of the curcuminoid mixture.

In some embodiments, a bioavailable curcumin formulation enhances lymphatic bioavailability of curcumin. In some embodiments, a bioavailable curcumin formulation enhances bioavailability of curcumin in blood.

The composition of disclosed curcuminoid mixtures having higher curcumin-keto compound is in a dosage form chosen from oral, parenteral, topical and transdermal forms. The oral dosage form can be tablets, capsules, soft gel capsules, granules, powders, lozenges, syrups, elixirs, solutions, or suspensions. The topical dosage form can be powders, sprays, ointments, pastes, creams, lotions, gels, solutions, patches or inhalants. The transdernmal dosage form can be powders, sprays, ointments, pastes, creams, lotions, gels, solutions, patches or inhalants.

The bioavailable curcumin formulations are in dosage forms chosen from oral, parenteral, topical and transdermal forms. The oral dosage form can be tablets, capsules, soft gel capsules, granules, powders, lozenges, syrups, elixirs, solutions, or suspensions. The topical dosage form can be powders, sprays, ointments, pastes, creams, lotions, gels, solutions, patches or inhalants. The transdermal dosage form can be powders, sprays, ointments, pastes, creams, lotions, gels, solutions, patches or inhalants.

A dosage form of the disclosed compositions having curcuminoid mixture alone (with higher amount of curcumin-keto compound as compared to curcumin-keto found in turmeric rhizomes) are administered in a dosage ranging from about 100 mg to about 2000 mg per day to a human subject.

A dosage form of the disclosed bioavailable curcumin formulations is administered in a dosage ranging from about 100 mg to about 2000 mg per day to a human subject.

Some embodiments provide a method of administering the disclosed curcuminoid mixtures to a subject in need thereof. Some embodiments provide a method of administering the disclosed bioavailable curcumin formulations to a subject in need thereof.

Some embodiments provide a method of treatment by administering the disclosed curcuminoid mixtures to a subject in need thereof. Some embodiments provide a method of treatment by administering the disclosed bioavailable curcumin formulations to a subject in need thereof.

It will be readily understood by the skilled artisan that numerous alterations may be made to the examples and instructions given herein. These and other objects and features of present invention will be made apparent from the following examples. The following examples as described are not intended to be construed as limiting the scope of the present invention.

EXAMPLES

Example 1

Method of Preparation of Curcuminoid Mixture Alone (Also Referred to as "Regular Turmeric Extract")

Kg turmeric rhizomes were dried and powdered to form powdered turmeric. The powdered turmeric was treated with 900 L ethyl acetate to form a solution. The extraction was carried out at 78° C. temperature for 1 hr. After initial extraction, the extraction process was repeated 4 more times and the resultant solution was filtered and the solvent was stripped from the filtered solution to form an extract. This extract was cooled to about 4° C. to obtain crystals of curcuminoid (12 Kg) and a liquid. The crystals of curcuminoid were isolated from the liquid by filtration. The crystals were powdered to form powdered curcuminoid mixture. About 95% of the powdered curcuminoid mixture was composed of curcuminoid mixture and the remaining 5% of the powdered curcuminoid mixture included trace amounts of essential oil of turmeric, and other components such as carbohydrates and proteins. The powdered curcuminoid mixture is also referred to as 95% curcuminoids, regular turmeric extract or curcuminoid mixture alone. The powdered curcuminoid mixture had curcumin-keto compound, curcumin-enol compound, demethoxycurcumin and bisdemethoxycurcumin. The ratio of curcumin-keto compound to curcumin-enol compound in the powdered curcuminoid mixture was about 0.09:0.91.

Example 2

Method of Preparation of Essential Oil of Turmeric with Varying Concentration of Ar-Turmerone Kg turmeric rhizomes were dried and powdered to form powdered turmeric. The powdered turmeric was treated with 1500 L of ethyl acetate to form a solution. The extraction was carried out at 78° C. temperature for 1 hr. After initial extraction, the extraction process was repeated 4 more times and the resultant solution was filtered and the solvent was stripped from the filtered solution to form an extract. This extract was cooled to about 4° C. to obtain crystals of curcuminoid mixture (20 Kg) and a liquid. The crystals of curcuminoid mixture were isolated from the liquid by filtration.

The remaining liquid had essential oil of turmeric and a resin. The liquid was then steam distilled to isolate essential oil of turmeric with 10-15% Ar-turmerone (25 Kg). After fractionating this oil, essential oil with 45% Ar-turmerone (7.5 Kg) was obtained as fraction 3 at 140° C., essential oil of turmeric with 4-5% Ar turmerone (8.3) was obtained as fraction 2 at 125° C. and essential oil of turmeric with 2-3% Ar turmerone (9.3 Kg) was obtained as fraction 1 at 110° C.

Example 3

Method of Preparation of Control Physical Blend (Sample 1) of Curcuminoid Mixture (Regular Turmeric Extract) and Essential Oil of Turmeric Having 45% Ar Turmerone in 15:1 Ratio.

9.1 Kg powder of curcuminoid mixture (also referred to as regular turmeric extract, or powdered curcuminoid mixture, or curcuminoid mixture alone, or 95% curcuminoids prepared as in Example 1) was blended with 0.6 kg of essential oil containing 45% Ar-turmerone by weight of the essential oil of turmeric, in a 15:1 ratio of curcuminoid mixture:essential oil of turmeric, to form a control physical blend of curcuminoid mixture (regular turmeric extract (not refluxed) blended with essential oil of turmeric having 45% Ar turmerone). The control physical blend is also referred to as Sample 1. In the method of preparation of control physical blend (Sample 1), no water was added to the regular turmeric extract and no refluxing step of refluxing the regular turmeric extract in water was performed prior to blending of the regular turmeric extract and essential oil of turmeric. In the control physical blend (Sample 1), the ratio of curcumin-keto compound to curcumin-enol compound was about 0.09:0.91.

Example 4

Method of Preparing Curcuminoid Mixture Having Curcumin-Keto to Curcumin-Enol in Ratio of 0.15:0.85

Kg turmeric rhizomes were dried and powdered to form powdered turmeric. The powdered turmeric was treated with 1500 L of ethyl acetate to form a solution. The extraction was carried out at 78° C. temperature for 1 hr. After initial extraction, the extraction process was repeated 4 more times and the resultant solution was filtered and the solvent was stripped from the filtered solution to form an extract. This extract was cooled to about 4° C. to obtain crystals of curcuminoid mixture (20 Kg) and a liquid. The crystals of curcuminoid mixture were isolated from the liquid by filtration.

Kg of curcuminoid mixture was suspended in 136 L water to form a suspension. The suspension was refluxed at about 95° C. for about 4 hrs to obtain a refluxed curcuminoid mixture. Water was evaporated from the refluxed curcuminoid mixture under vacuum and at about 60° C. till volume of the refluxed curcuminoid mixture was decreased to half of the starting quantity (68 L) of curcuminoid mixture for refluxing to obtain an evaporated refluxed curcuminoid mixture. The evaporated refluxed curcuminoid mixture was dried under vacuum at about 65° C. to obtain a curcuminoid mixture comprising a curcumin-keto compound, a curcumin-enol compound, a bisdemethoxycurcumin, and a demethoxycurcumin, and wherein a ratio of the curcumin-keto compound to the curcumin-enol compound was about 0.15:0.85 by weight.

Example 5

Method of Preparation of Bioavailable Turmeric Formulation (Sample 2), which is a Blend of Regular Turmeric Extract (Refluxed and Essential Oil of Turmeric Having 45% Ar Turmerone in 15:1 Ratio.

Kg powder of curcuminoid mixture (also referred to as regular turmeric extract, or curcuminoid mixture alone, or 95% curcuminoids, having a ratio of curcumin-keto compound to curcumin-enol compound of about 0.09:0.91, and prepared as described in Example 1) was suspended in 136 L water to form a suspension. The suspension was refluxed at 95° C. for 4 hrs. Subsequently, the water was evaporated under vacuum at 60° C. until the volume reached 68 L to obtain an evaporated mixture. Following this, 0.6 Kg of essential oil containing 45% Ar-turmerone (by weight of essential oil of turmeric) was added to the evaporated refluxed curcuminoid mixture to prepare a blend. The blend was then dried under vacuum at 65° C. to form the bioavailable curcumin formulation (also referred to as Sample 2) having a ratio of curcuminoid mixture and essential oil of turmeric of about 15:1 ratio. In this bioavailable curcumin formulation blend, the ratio of curcumin-keto compound to curcumin-enol compound was about 0.15:0.85.

Example 6

Keto-Enol Tautomerism of Curcumin in the Composition of Bioavailable Curcumin Formulation (Curcuminoid Mixture Refluxed in Water and then Blended with Essential Oil of Turmeric) Compared to Control Physical Blend (Curcuminoid Mixture without Adding Water or Refluxing Before Blending with Essential Oil of Turmeric)

Curcumin can exist in two primary forms: the keto form and the enol form, which are tautomeric forms of each other. In the keto form, curcumin has a diketone structure, meaning it contains two ketone functional groups (—C=O) at specific positions. The enol form of curcumin occurs when there is a shift in the arrangement of the hydrogen and oxygen atoms within the molecule. This shift results in the formation of an enol functional group (—C—OH) instead of a ketone. Naturally occurring curcumin in turmeric rhizomes exists primarily in an enol form.

The presence of keto and enol form of curcumin in regular turmeric extract (curcuminoid mixture alone, as prepared in Example 1) was confirmed by HPLC as shown in the HPLC chromatogram in FIG. 1. Y-axis in FIG. 1 shows absorbance unit (AU).

The peak of curcumin in enol form occurred at retention time 3.27 minutes, and the peak of curcumin in keto form was at retention time 1.26 minutes.

Figure 2:
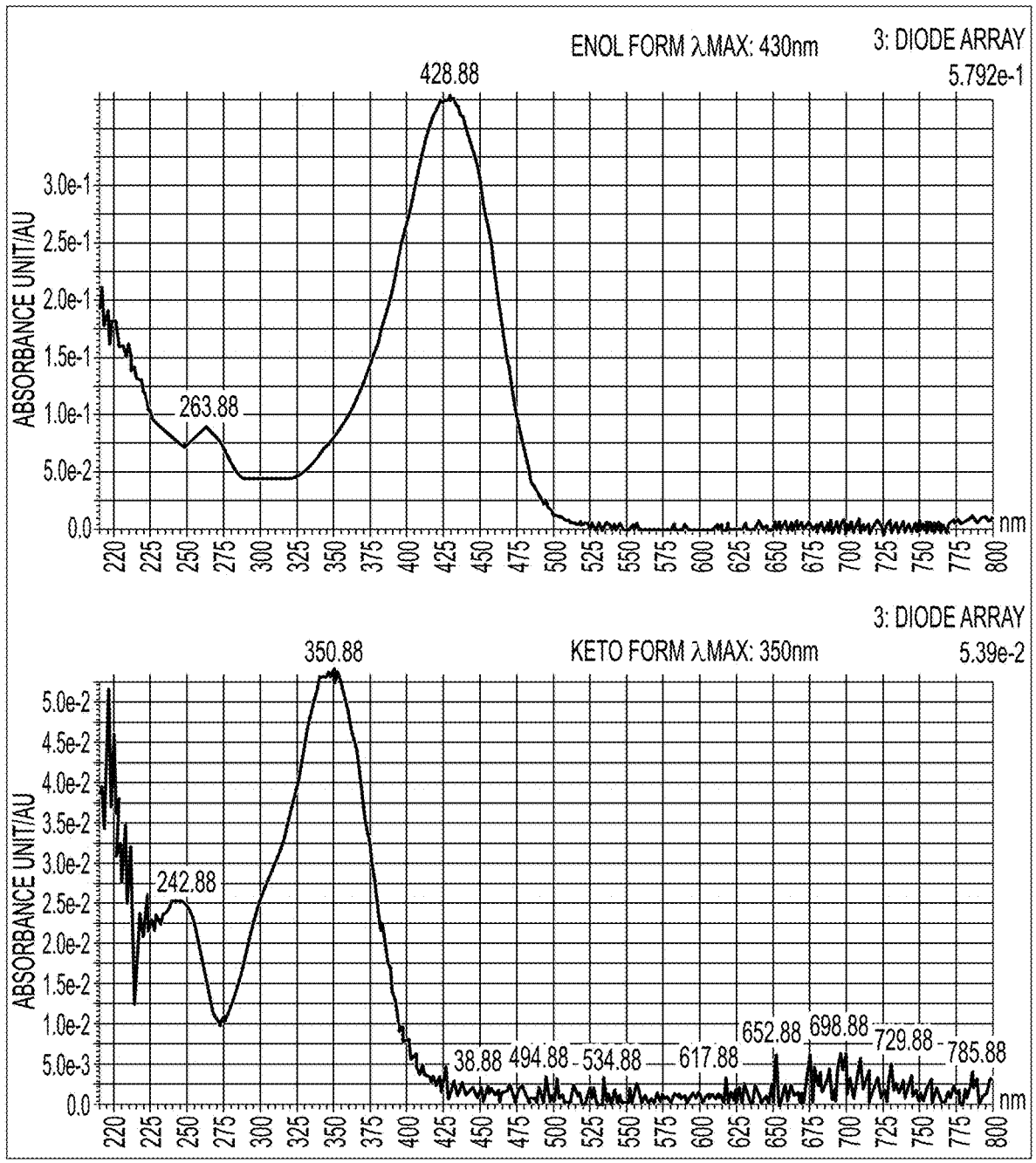
FIG. 2 represents HPLC chromatogram of showing absorption maxima of curcumin keto form at 350 and curcumin-enol form at 428 nm by HPLC method in regular turmeric extract (curcuminoid mixture alone).

The absorption maxima and mass of keto and enol forms of curcumin in regular turmeric extract (curcuminoid mixture alone, as prepared in Example 1) was analyzed by HPLC and its results again confirmed the presence of keto form and enol form of curcumin in regular turmeric extract (curcuminoid mixture alone). HPLC chromatogram showed absorption maxima of enol form was 428.88 nm and keto form was 350.88 nm (FIG. 2).

Figure 3:
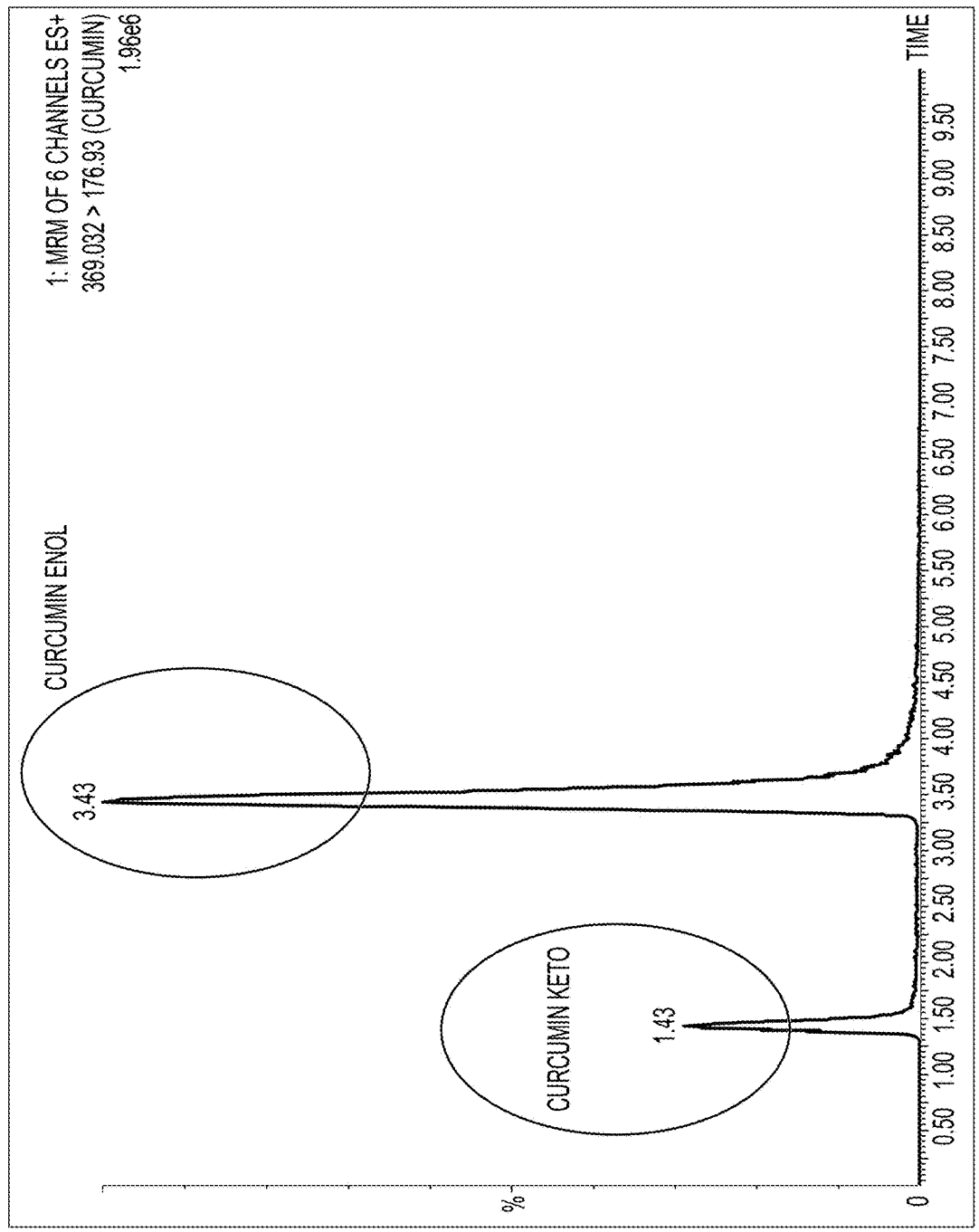
FIG. 3 represents Liquid Chromatography Tandem Mass Spectrometry (LCMS/MS) spectra of enol and keto form of curcumin in regular turmeric extract (curcuminoid mixture alone).

The LCMS/MS spectra of enol and keto forms of curcumin in curcuminoid mixture alone (without refluxing) showed the fragmentation mass of Enol form was 175 and keto form was 176 (FIG. 3).

Curcumin-Keto: curcumin-enol ratios in different samples were analyzed by UPLCMS/MS.

Sample 1—Physical blend (control) of regular turmeric extract (curcuminoid mixture alone without refluxing) and essential oil of turmeric (Example 3).

Sample 2—Bioavailable curcumin formulation of Curcuminoid mixture (refluxed in water) blended with Essential oil of turmeric (Example 5).

Figure 4A:
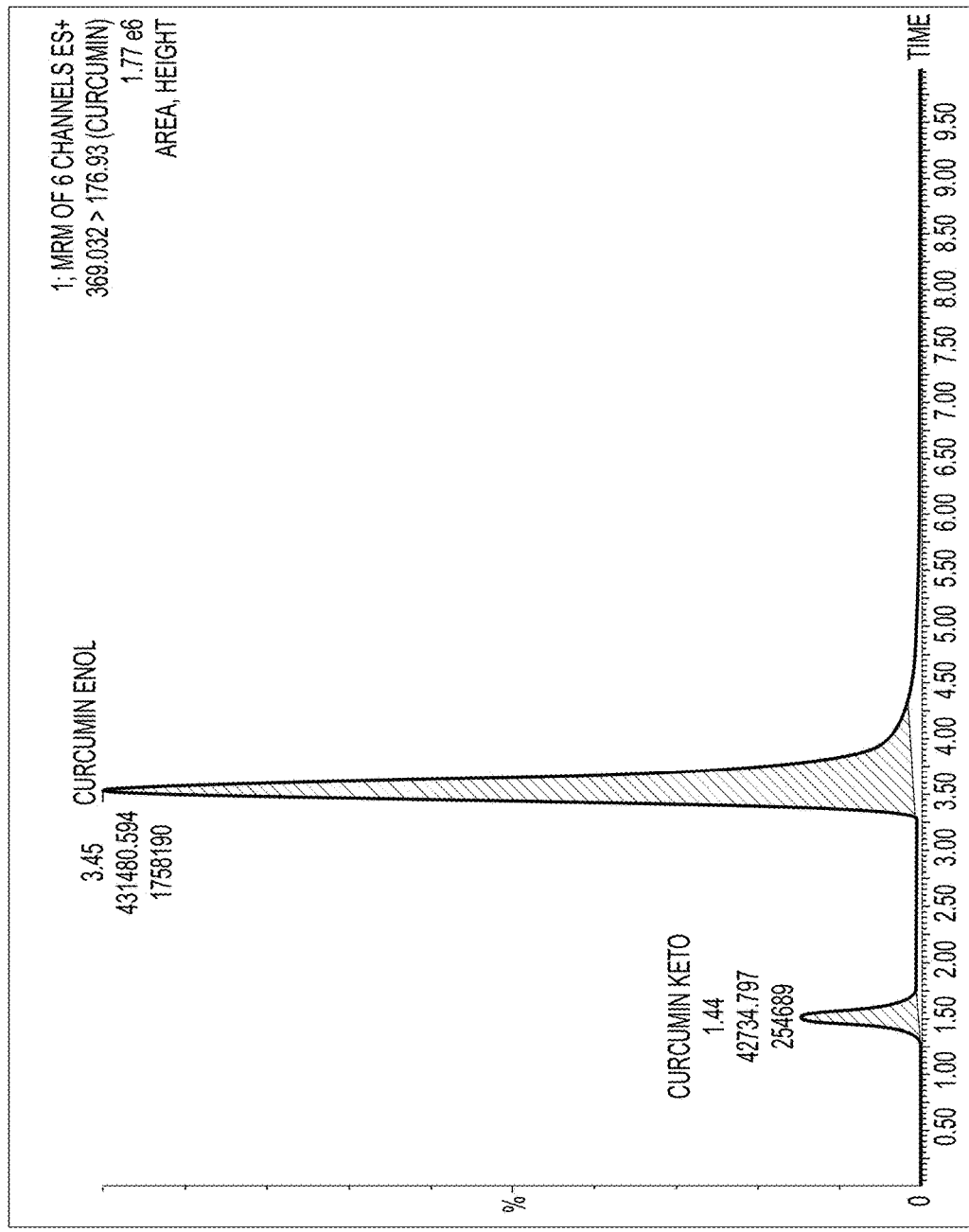
FIG. 4A represents Ultra-Performance Liquid Chromatography Tandem Mass Spectrometry (UPLCMS/MS) chromatogram of Sample 1 (Control physical blend).
Figure 4B:
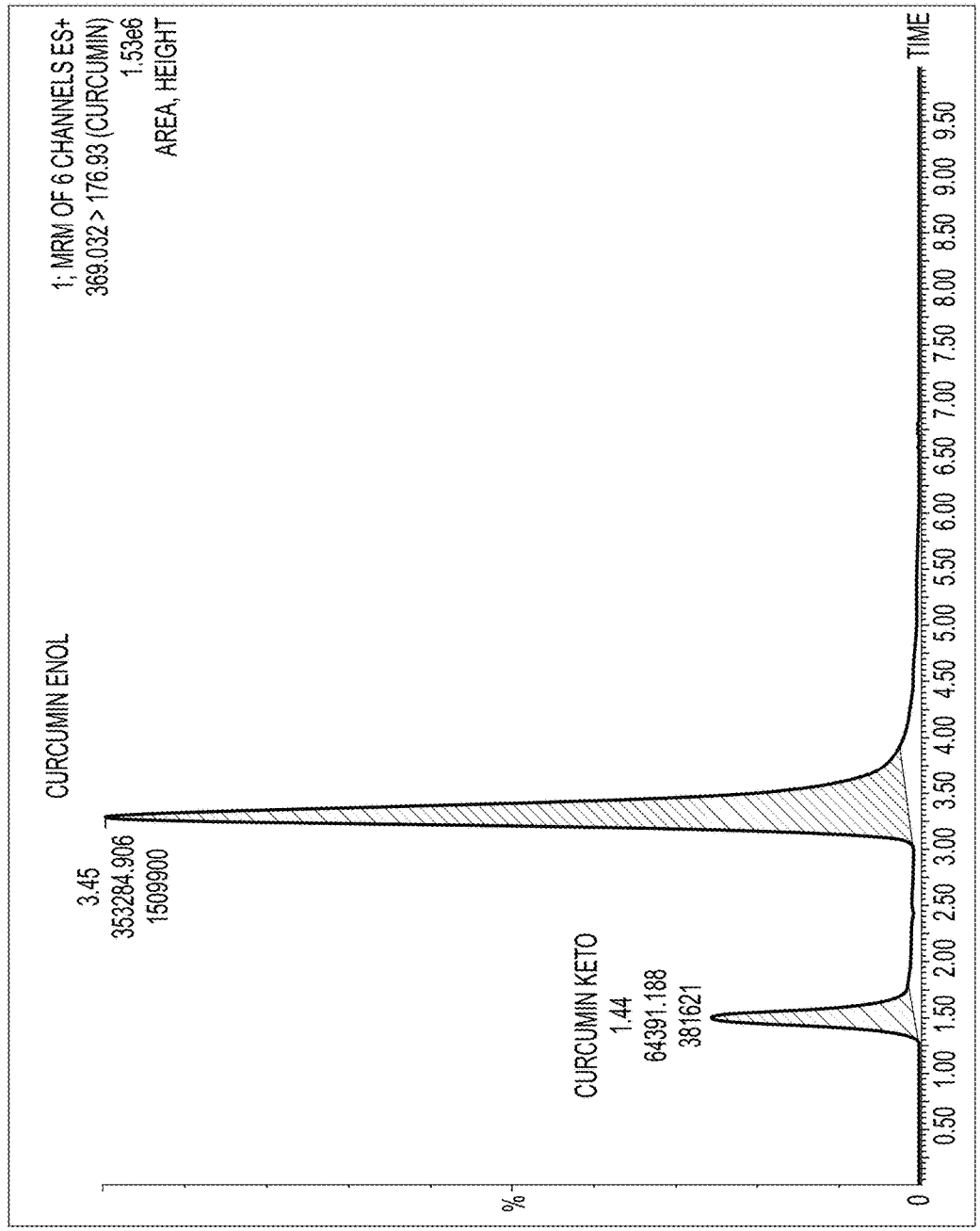
FIG. 4B represents Ultra-Performance Liquid Chromatography Tandem Mass Spectrometry (UPLCMS/MS) chromatogram of Sample 2 (Bioavailable curcumin formulation).

Samples for UPLCMS/MS analysis were prepared in Acetonitrile: 0.1% Formic acid (1:1) and 5 μl samples were injected for UPLCMS/MS analysis. The chromatogram obtained for Sample 1 and Sample 2 is represented in FIG. 4A and FIG. 4B respectively.

In Sample 1, which was the control physical blend of regular turmeric extract (curcuminoid mixture alone) and essential oil of turmeric, the observed ratio of curcumin Keto compound:curcumin-Enol compound was 0.09:0.91 (based on ratio of keto and enol peak areas), whereas for Sample 2, the ratio between Keto:Enol was 0.15:0.85. Comparing the ratios of Sample 1 and Sample 2 showed that there was a 50% increase in keto and 18% decrease in Enol tautomer in Sample 2. The preparation of Sample 2 required addition of water to the regular turmeric extract followed by refluxing before blending with the essential oil of turmeric and these steps were not performed in the preparation of the control physical blend (Sample 1).

From the above analysis it is clear that the composition of bioavailable curcumin formulation containing curcuminoid mixture (refluxed with water) and blended with essential oil of turmeric showed higher keto form of curcumin as compared to a Control physical blend of regular turmeric extract (curcuminoid mixture which was not refluxed with water) and essential oil of turmeric.

Example 7

SEM analysis of bioavailable curcumin formulation (Curcuminoid mixture refluxed in water and blended with Essential oil of turmeric) as compared to control physical blend (curcuminoid mixture and essential oil of turmeric)

Scanning electron microscopy (SEM) is used for surface morphological and topographical studies and also for compositional elemental analysis. Two samples were taken for SEM analysis.

Sample 1—Physical blend (control) of curcuminoid mixture (regular turmeric extract) and essential oil of turmeric.

Sample 2—Bioavailable curcumin formulation of Curcuminoid mixture (refluxed with water) blended with Essential oil of turmeric.

SEM analysis of above two samples were done by placing the sample stub with each sample onto the SEM sample stage. Imaging mode was selected and images were captured at different magnification using SEM's software. Samples were analyzed at 150×, 500×, 1500× and 3500× magnification.

Figure 5A:
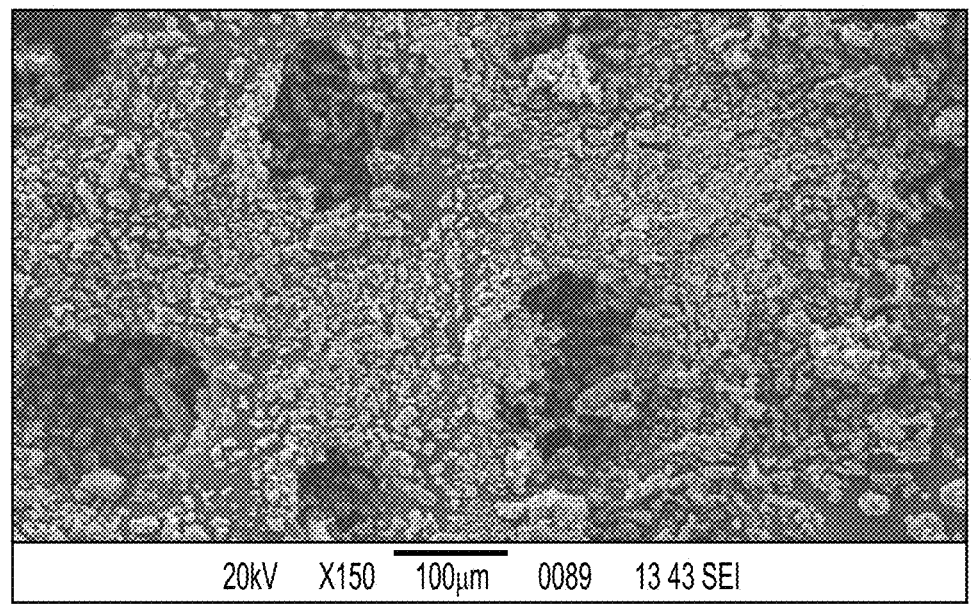
FIG. 5A represents Scanning Electron Microscopy (SEM) images of sample 1 (Control physical blend) at ×150 magnification.
Figure 5B:
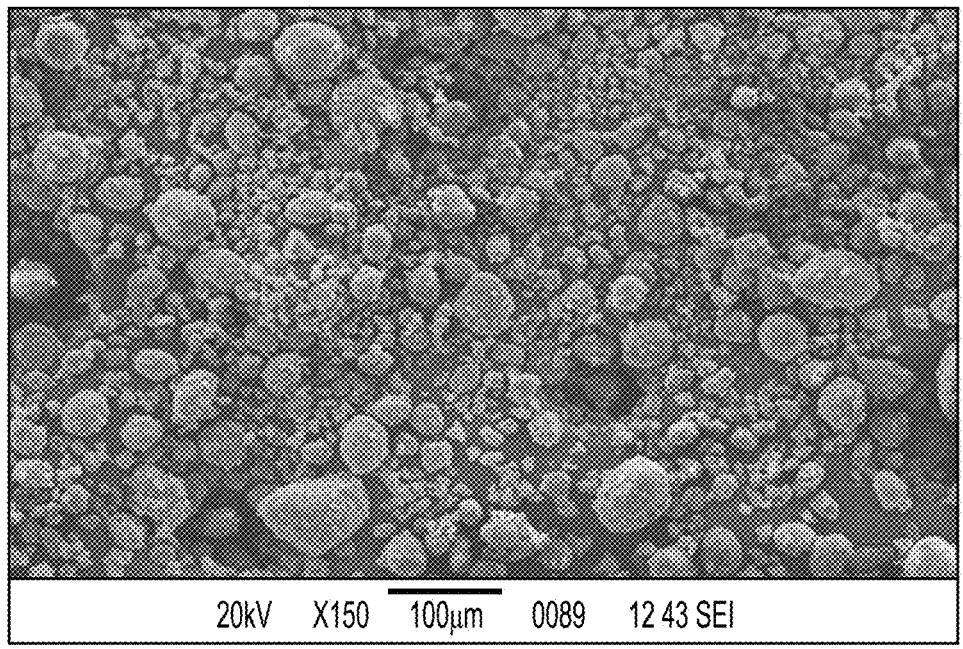
FIG. 5B represents SEM image of Sample 2 (Bioavailable curcumin formulation) at ×150 magnification.
Figure 6A:
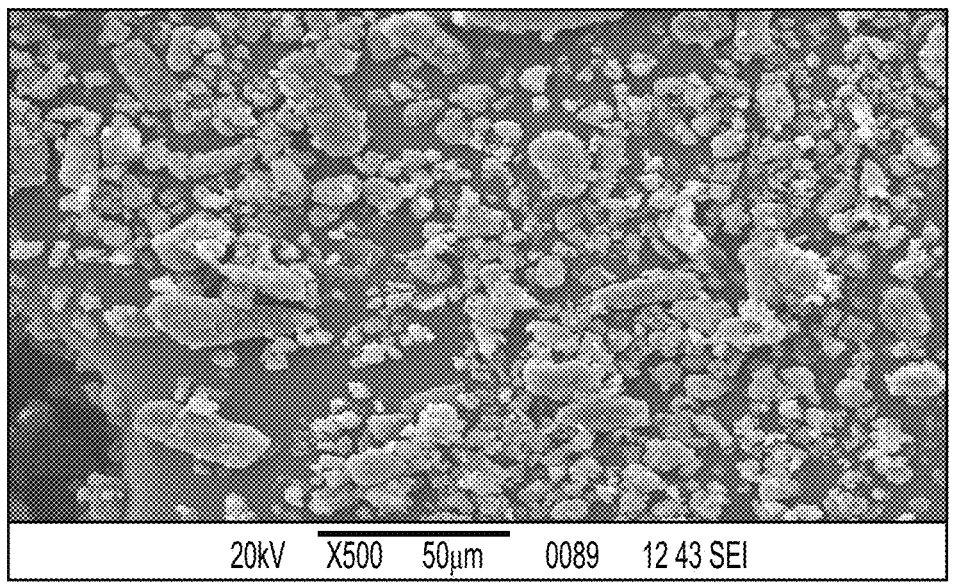
FIG. 6A represents SEM image of sample 1 (Control physical blend) at ×500 magnification.
Figure 6B:
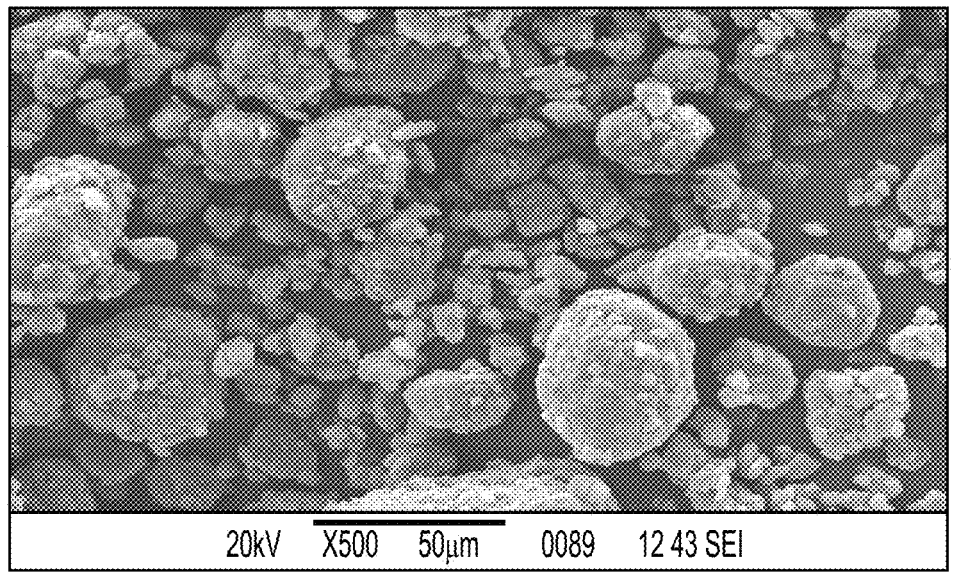
FIG. 6B represents SEM image Sample 2 (Bioavailable curcumin formulation) at ×500 magnification.
Figure 7A:
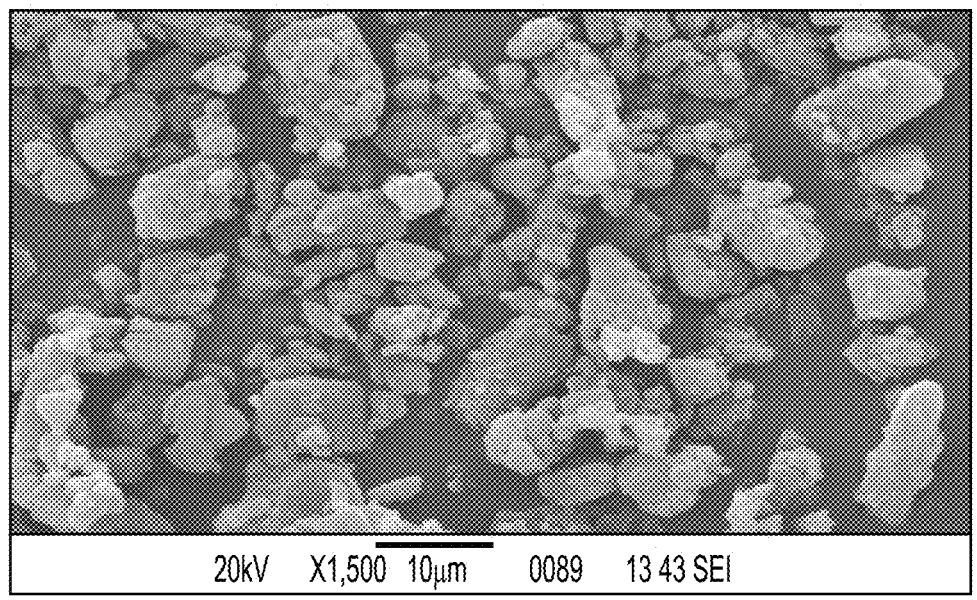
FIG. 7A represents SEM images of Sample 1 (Control physical blend) at ×1500 magnification.
Figure 7B:
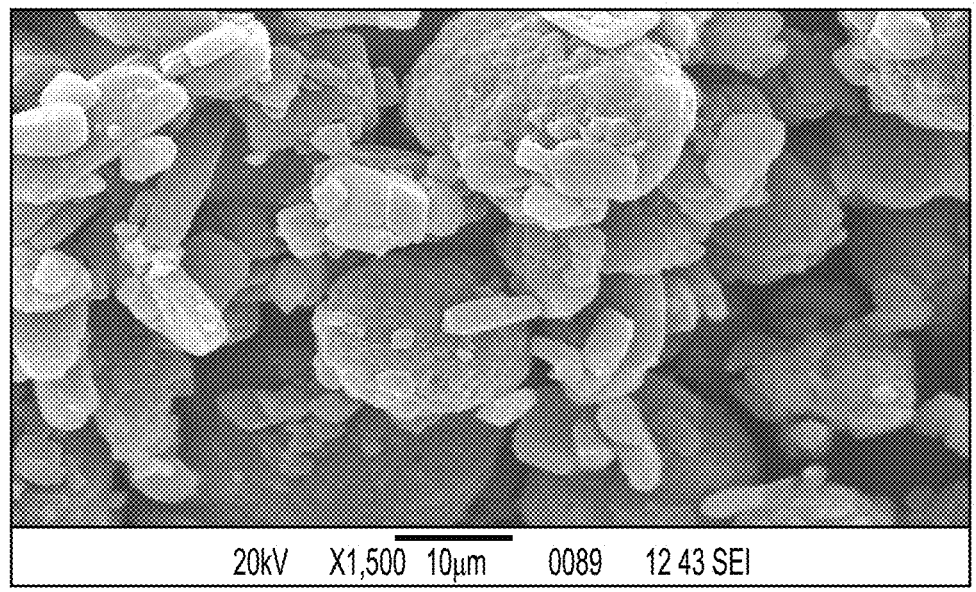
FIG. 7B shows Sample 2 (Bioavailable curcumin formulation) at ×1500 magnification.
Figure 8A:
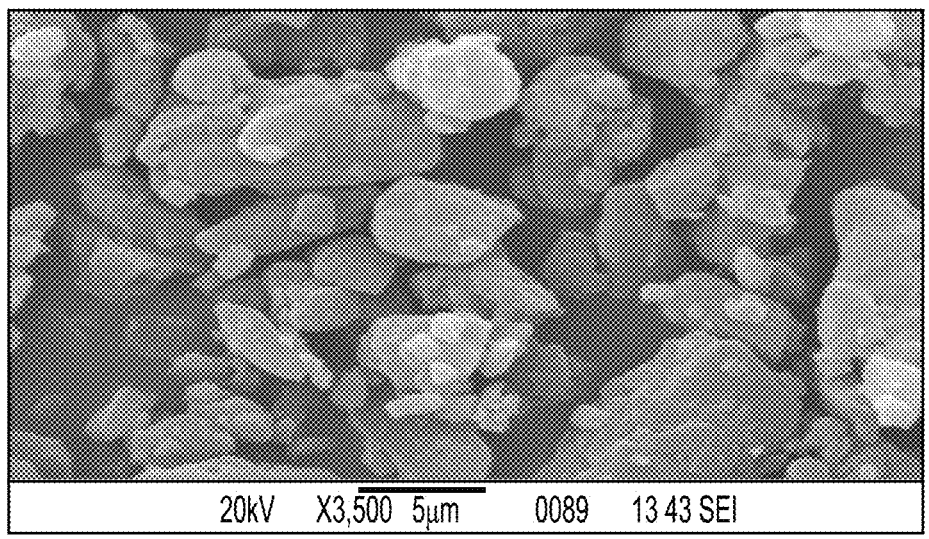
FIG. 8A represents SEM image of Sample 1 (Control physical blend) at ×3500 magnification.
Figure 8B:
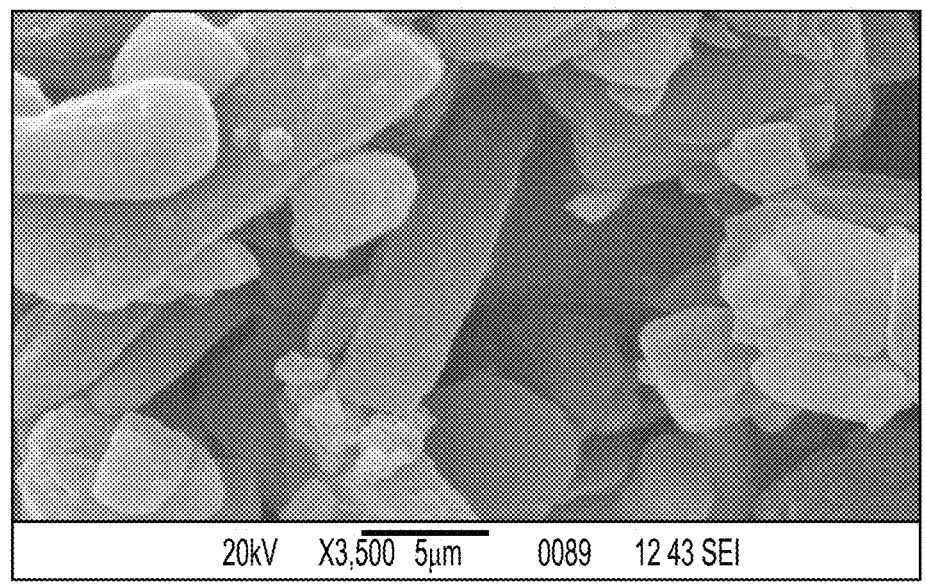
FIG. 8B shows SEM image of Sample 2 (Bioavailable curcumin formulation) at ×3500 magnification.
Figure 9B:
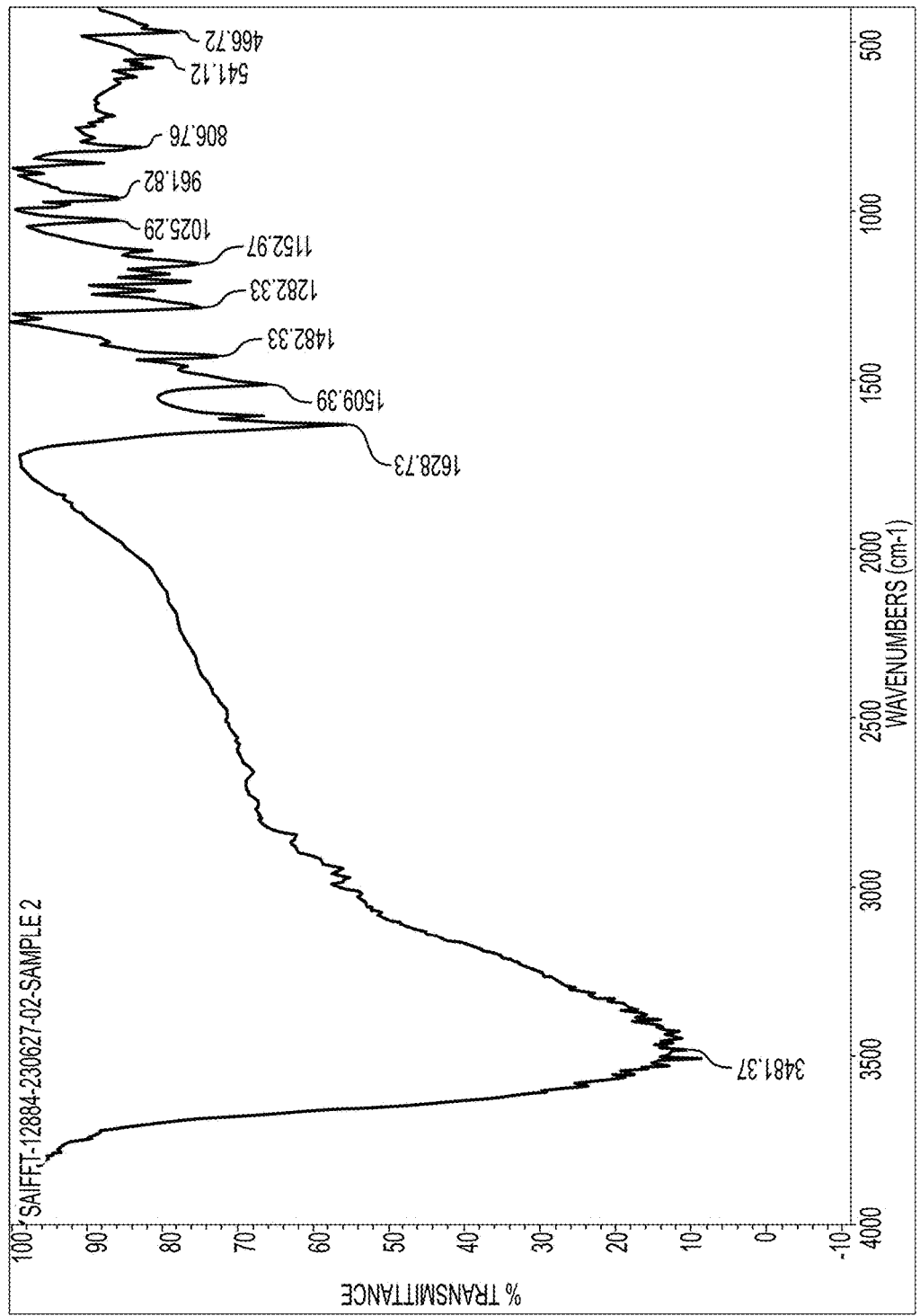
FIG. 9B shows FTIR spectra of Sample 2 (Bioavailable curcumin formulation).

SEM Images of sample 1 and Sample 2 at different magnification was represented as FIGS. 5A and 5B respectively (SEM images at ×150 magnification), FIGS. 6A and 6B respectively (SEM images at ×500 magnification), FIGS. 7A and 7B respectively (SEM images at ×1500 magnification) and FIGS. 8A and 8B respectively (SEM images at ×3500 magnification).

There was a distinct difference in the SEM images of bioavailable curcumin formulation of curcuminoid mixture prepared by refluxing with water and essential oil of turmeric (Sample 2) as compared to control physical blend (Sample 1). The difference could be due to the formation of aggregates and more crystalline nature of the products observed in sample 2.

In the presence of water, curcumin is known to form clusters in a very definite pattern where they tend to aggregate both in parallel and anti-parallel orientation of the phenyl rings. Such parallel alignment leads to a more closely packed cluster with maximum number of hydrophobic contacts.

Sample 2 might be a metastable structural intermediate involving a number of intermediate-sized clusters dispersed in the solution. Once we removed water from its sequestered hydrophobic core, the final aggregated form remained stable.

Example 8

Evaluation of absorption of curcumin in lymph and blood after administering bioavailable curcumin formulation.

New Zealand male rabbits weighing 1.8-2 Kg were selected and rabbits were divided into four groups containing 6 rabbits in each group.

Group 1: Rabbits fed with bioavailable curcumin formulation (Sample 2 prepared as in Example 5 and having curcumin-keto compound: curcumin-enol compound at a 0.15:0.85 ratio) at a dosage of 100 mg/Kg bodyweight.

Group 2: Rabbits fed with control physical blend of regular turmeric extract (Sample 1 prepared as in Example 3 and having curcumin-keto compound: curcumin-enol compound at a 0.09:0.91 ratio) at a dosage of 100 mg/Kg bodyweight.

Group 3: Rabbits fed with regular turmeric extract (curcuminoid mixture alone having curcumin-Keto compound: curcumin-enol compound at a ratio 0.09:0.91 prepared as in Example 1) at a dosage of 100 mg/Kg bodyweight.

Group 4: Rabbits fed with control sample (regular turmeric extract suspended in water and then blended with essential oil of turmeric; resulting in curcumin-Keto compound: curcumin-enol compound at a ratio 0.10:0.90) at a dosage of 100 mg/Kg bodyweight.

Animals were anesthetized and abdomen was exposed by making an incision along the midline. The transparent lymph vessel was identified and catheter was carefully inserted in to the lymph vessel through a minute incision. Animals were allowed to recover for 24 hrs after the surgical procedures.

Group 1, Group 2, Group 3 and Group 4 animals were administered bioavailable curcumin formulation, control physical blend of regular turmeric extract and essential oil of turmeric, regular turmeric extract, curcuminoid mixture suspended in water and then blended with essential oil of turmeric (having 45% ar-turmerone) orally at the dose of 100 mg/kg body weight of the animals. After the administration with the test samples, blood (0.2 ml to 0.3 ml) was collected through marginal ear vein at 0 min (immediately after the test compound administration), 30 min, 1 hour, 2 hours, 4 hours, 8 hours, 12 hours, 16 hours, 20 hours and 24 hrs of post dose. Lymphatic fluid (0.1 ml to 0.2 ml) were collected through cannulated lymph vessel at 0 min (immediately after the test compound administration), 30 min, 2 hours, 8 hours, and 24 hrs of post dose.

Curcumin concentration in the lymphatic fluid and blood were analysed by LCMS method.

TABLE 1

Absorption of curcumin (ng/lymph) in Lymph

| Time (Hr) | Group 1 Bioavailable curcumin formulation (Sample 2) | Group 2 Physical blend (control, Sample 1) | Group 3 curcuminoid mixture alone (control) | Group 4 Curcuminoid mixture suspended in water + EOT (suspension control) |
|---|---|---|---|---|
| 0 | 0 | 0 | 0 | 0 |
| 0.5 | 25.5 | 14.2 | 6.5 | 18.2 |
| 2 | 52.1 | 10.2 | 2.1 | 9.2 |
| 8 | 34.8 | 2.7 | 0 | 3 |
| 24 | 12.2 | 0 | 0 | 0 |

Figure 12:
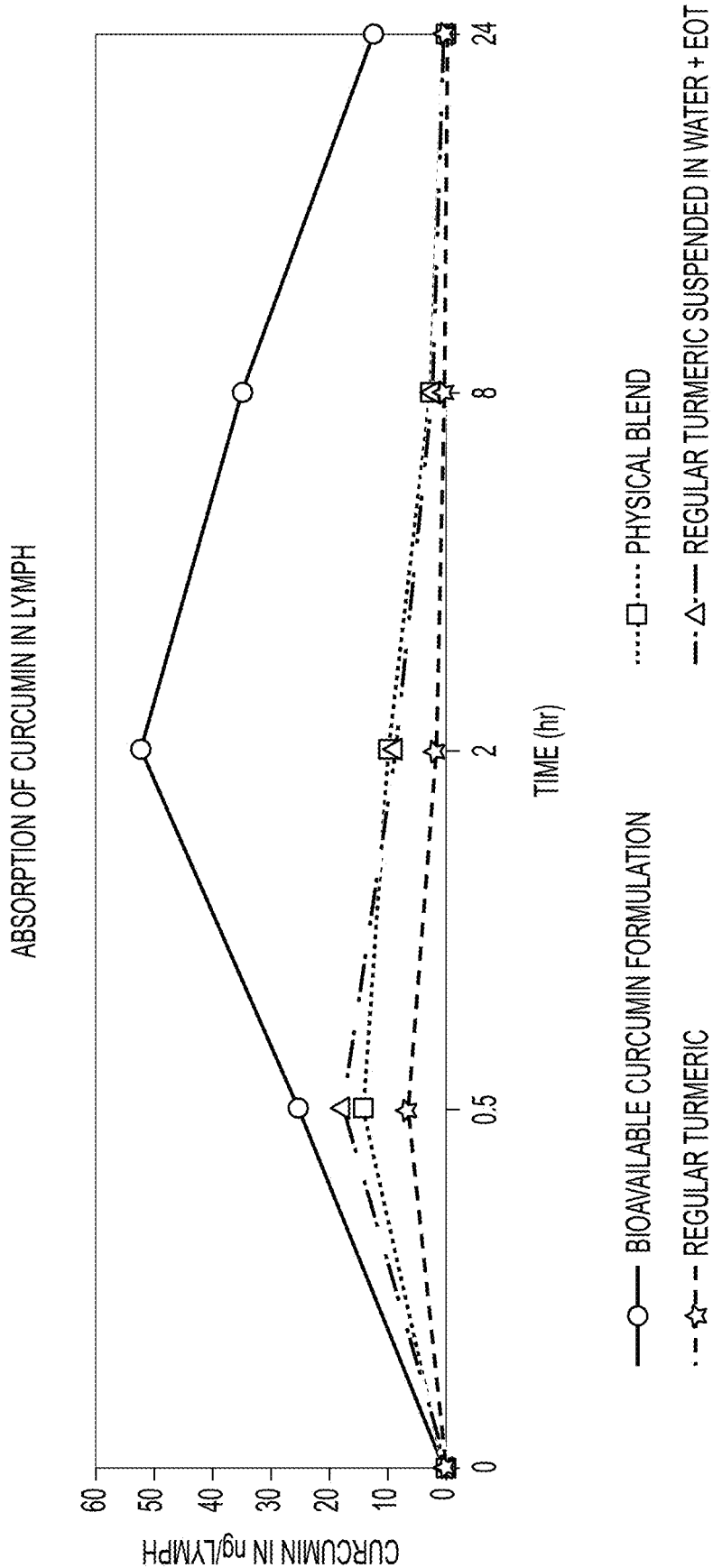
FIG. 12 shows bioavailability of curcumin in lymph following administration of bioavailable curcumin formulation (Sample 2; open circles), control physical blend (Sample 1; open squares) regular turmeric extract (curcuminoid mixture alone; open triangles).

The results in Table 1 indicate that after administering bioavailable curcumin formulation to Group 1 animals, the peak absorption of curcumin was 52.1 ng/lymph occurred at 2 hours and curcumin was detected in lymph for up to 24 hrs. Following administration of control physical blend (regular turmeric extract and essential oil of turmeric) to Group 2 animals, a maximum absorption of curcumin 14.2 ng/lymph occurred at 0.5 hour and curcumin was detected upto 8 hours. Regular turmeric extract (curcuminoid mixture alone) administered to Group 3 animals showed a maximum absorption of 6.5 ng/lymph curcumin at half an hour, and curcumin was detected only up to 2nd hour. Group 4 animals administered with Regular turmeric extract suspended in water and mixed with essential oil of turmeric (control sample) showed a maximum absorption of 18.2 ng/lymph which occurred at 0.5 hour. The data from Table 1 is provided in graph in FIG. 12.

The results demonstrate that the bioavailable curcumin formulation (Sample 2) showed superior results for absorption of curcumin in lymph and for a longer duration of time as compared to a control physical blend (curcuminoid mixture alone and essential oil of turmeric without refluxing or suspension of curcuminoid mixture in water), or as compared to a control having curcuminoid mixture alone, or a control prepared with curcuminoid mixture alone and essential oil of turmeric with suspension of curcuminoid mixture in water prior to adding essential oil of turmeric. The fold increase in curcumin absorption in lymph following Sample 2 administration was about 3.7 fold as compared to control physical blend. The fold increase in curcumin absorption in lymph following Sample 2 administration was about 8 fold as compared to curcuminoid mixture alone.

TABLE 2

Absorption of curcumin (ng/ml) in Blood.

| Time (Hr) | Group 1 Bioavailable curcumin formulation (Sample 2) | Group 2 Physical blend (control, Sample 1) | Group 3 curcuminoid mixture alone (control) | Group 4 Curcuminoid mixture suspended in water + EOT (suspension control) |
|---|---|---|---|---|
| 0 | 0 | 0 | 0 | 0 |
| 0.5 | 21.1 | 6.1 | 5.5 | 7.2 |
| 1 | 29.3 | 11.3 | 4 | 15.9 |
| 2 | 43.2 | 8.4 | 1.9 | 10.2 |
| 4 | 34.2 | 4.2 | 1 | 6.1 |
| 8 | 26.9 | 1.5 | 0 | 3 |
| 12 | 18.2 | 0 | 0 | 1.2 |
| 16 | 15.1 | 0 | 0 | 0 |
| 20 | 10.1 | 0 | 0 | 0 |
| 24 | 7.3 | 0 | 0 | 0 |

Figure 13:
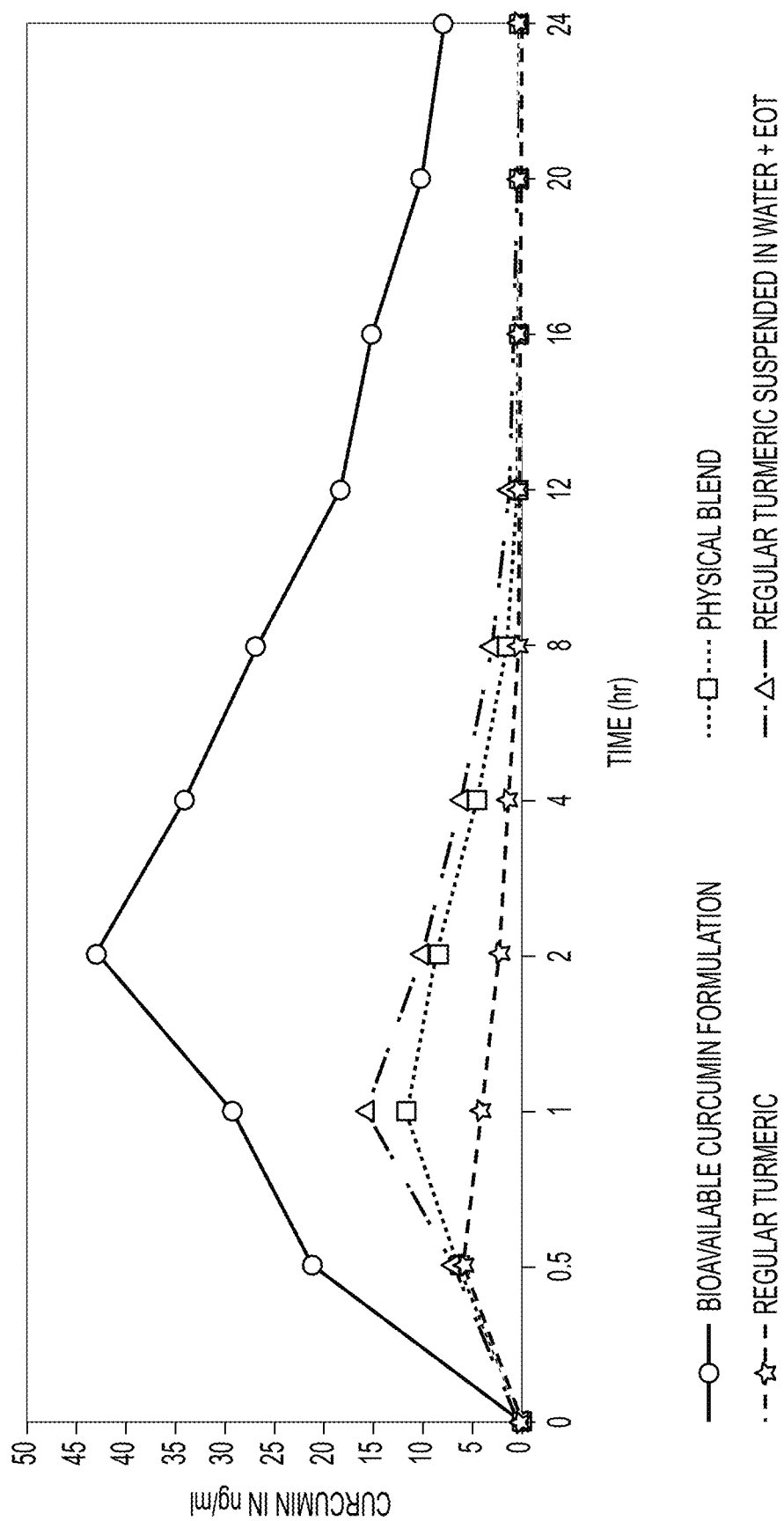
FIG. 13 shows bioavailability of curcumin in blood following administration of bioavailable curcumin formulation (Sample 2; open circles), control physical blend (Sample 1; open squares) regular turmeric extract (curcuminoid mixture alone; open triangles).

The results from Table 2 indicate that after administering bioavailable turmeric formulation (Sample 2) to Group 1 animals, the peak absorption of curcumin in blood was 43.2 ng/ml occurred at 2nd hour and curcumin was detected in blood up to 24 hrs. Administration of control physical blend (regular turmeric extract and essential oil of turmeric; Sample 1) to Group 2 animals showed a maximum absorption of curcumin in blood of 11.3 ng/ml which occurred at 1st hour. Detection of curcumin was noted up to 8 hours. Regular turmeric extract (curcuminoid mixture alone) administered to group 3 animals showed an absorption of 5.5 ng/ml blood at half an hour and curcumin was detected only up to 4th hour. Group 4 animals administered with Regular turmeric extract suspended in water and mixed with essential oil of turmeric (control sample) showed a maximum absorption of curcumin in blood of 15.9 ng/ml which occurred at 1st hour. The data from Table 2 is provided in graph in FIG. 13.

The results demonstrate that the bioavailable curcumin formulation (Sample 2) showed superior results for absorption of curcumin in blood and was available for a longer duration of time as compared to a control physical blend (curcuminoid mixture alone and essential oil of turmeric) or as compared to a control having curcuminoid mixture alone, or a control prepared with curcuminoid mixture alone and essential oil of turmeric with suspension of curcuminoid mixture in water prior to adding essential oil of turmeric. The fold increase in curcumin absorption in blood following Sample 2 administration was about 3.8 fold as compared to control physical blend. The fold increase in curcumin absorption in blood following Sample 2 administration was about 7.8 fold as compared to curcuminoid mixture alone.

Example 9

Surface Area Analysis of Bioavailable Curcumin Formulation (Curcuminoid Mixture Refluxed in Water and Blended with Essential Oil of Turmeric) Compared to Control Physical Blend (Curcuminoid Mixture and Essential Oil of Turmeric)

Surface area of two samples were analysed using BET surface area analyser.

Sample 1—Physical blend (control) of regular turmeric extract (curcuminoid mixture alone prepared without refluxing) and essential oil of turmeric having a curcumin-Keto compound: curcumin-enol ratio of 0.09:0.91 in the curcuminoid mixture. In Sample 1, the ratio of curcuminoid mixture to essential oil of turmeric was 15:1.

Sample 2—Bioavailable curcumin formulation of Curcuminoid mixture (refluxed in water) and Essential oil of turmeric, having a curcumin-Keto compound: curcumin-enol compound ratio of 0.15:0.85. In Sample 2, the ratio of curcuminoid mixture to essential oil of turmeric was 15:1.

About 0.1 gm of sample material was ground into a fine powder and thoroughly degassed below 120° C. for 5 hours to remove any adsorbed gases and moisture that might interfere with the analysis. Liquid nitrogen gas was introduced to the sample in a controlled environment. The gas was adsorbed onto the surface of the sample at various pressures. As the pressure of the adsorbate gas was increased, the quantity of gas adsorbed onto the sample was measured at each pressure point. This data was collected to create an adsorption isotherm. The BET equation was applied to the adsorption isotherm data. The equation relates the amount of gas adsorbed at each pressure to the monolayer capacity, the gas pressure, and a constant related to the adsorption energy. The specific surface area of each samples was determined.

TABLE 3

Surface area determination

| | BET surface area |
|---|---|
| Sample 1 (control physical blend) | 0.8429 $m^2/g$ |
| Sample 2 (bioavailable curcumin formulation) | 0.17787 $m^2/g$ |

Typically, a greater surface area tends to result in higher activity. A larger surface area provides more opportunities for interactions or reactions to occur. Greater surface area allows for more contact or exposure, leading to enhanced activity or efficiency. However, unexpectedly there was an exception to this general rule in the case of Sample 2, which exhibited lower surface area (0.17787 $m^2/g$; Table 3) as compared to control physical blend (Sample 1, 0.8429 m²/g; Table 3) yet showed higher bioavailability of curcumin in lymph (as shown in Example 9, Table 1) and in blood (as shown in Example 9, Table 2). This reduced surface area in Sample 2 might be attributed to the entrapment of essential oil within its pores. In contrast, Sample 1, which was physically blended, possessed a larger surface area. In the control physical blend, the oil was not effectively absorbed into the pores when compared to Sample 2.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

I claim:

1. A composition for enhanced bioavailability of curcumin in blood comprising a curcuminoid mixture and an essential oil of turmeric, wherein the curcuminoid mixture comprises a curcumin-keto compound, a curcumin-enol compound, a bisdemethoxycurcumin and a demethoxycurcumin, wherein a weight ratio of the curcumin-keto compound to the curcumin-enol compound ranges from about 0.12-0.20:0.8-0.88, and wherein the composition is a free-flowing powder.

2. The composition for enhanced bioavailability of curcumin in blood of claim 1, wherein the weight ratio for the curcumin-keto compound to the curcumin-enol compound is about 0.15: about 0.85.

3. The composition for enhanced bioavailability of curcumin in blood of claim 1, wherein the essential oil of turmeric comprises ar-turmerone.

4. The composition for enhanced bioavailability of curcumin in blood of claim 1, wherein the essential oil of turmeric comprises about 30% to about 60% ar-turmerone by weight.

5. The composition for enhanced bioavailability of curcumin in blood of claim 1, wherein a weight ratio of the curcuminoid mixture to the essential of turmeric ranges from about 5:1 to about 20:1 by weight.

6. The composition for enhanced bioavailability of curcumin in blood of claim 1, wherein the composition comprises a surface area ranging from about 0.05 to about 0.3 m²/g.

7. The composition for enhanced bioavailability of curcumin in blood of claim 5, wherein the composition comprises a surface area of about 0.17 m²/g.

8. The composition for enhanced bioavailability of curcumin in blood of claim 1 comprising a scanning electron microscopy (SEM) image chosen from FIG. 5B, FIG. 6B, FIG. 7B or FIG. 8B.

9. The composition for enhanced bioavailability of curcumin in blood of claim 1 comprising a Fourier Transform Infrared Spectroscopy (FTIR) spectra as presented in FIG. 9B.

10. The composition for enhanced bioavailability of curcumin in blood of claim 1 comprising a Nuclear Magnetic Resonance (NMR) spectra as presented in FIG. 10B.

11. The composition for enhanced bioavailability of curcumin in blood of claim 1 comprising a Matrix-Assisted Laser Desorption/Ionization Time-of-Flight (MALDI TOF) spectra as presented in FIG. 11B.

12. An oral dosage form comprising the composition for enhanced bioavailability of curcumin in blood of claim 1 chosen from tablet, capsule, soft gel capsule, granule, powder, lozenge, syrup, elixir, solution or suspension.

13. The composition for enhanced bioavailability of curcumin in blood of claim 1 prepared by a method, the method comprising:
suspending a curcuminoid mixture in about 10 to about 20 times water to form a suspension;
refluxing the suspension at about 70° C. to about 95° C. for about 0.5 hour to about 5 hrs to obtain a refluxed mixture;
evaporating water from the refluxed mixture under vacuum and at about 30° C. to about 60° C. till volume of the refluxed mixture is decreased to half to obtain an evaporated mixture;
adding essential oil of turmeric to the evaporated mixture to form a blend;
drying the blend under vacuum at about 30° C. to about 65° C. to obtain the composition for enhanced bioavailability of curcumin of claim 1.

14. A composition for enhanced lymphatic bioavailability of curcumin comprising a curcuminoid mixture and an essential oil of turmeric, wherein the curcuminoid mixture comprises a curcumin-keto compound, a curcumin-enol compound, a bisdemethoxycurcumin and a demethoxycurcumin, wherein a weight ratio of the curcumin-keto compound to the curcumin-enol compound ranges from about 0.12-0.20:0.8-0.88, and wherein the composition is a free-flowing powder.

15. The composition for enhanced lymphatic bioavailability of curcumin of claim 14, wherein the weight ratio of the curcumin-keto compound to the curcumin-enol compound is about 0.15:0.85.

16. The composition for enhanced lymphatic bioavailability of curcumin of claim 14, wherein the composition comprises a surface area ranging from about 0.05 to about 0.3 m²/g.

17. The composition for enhanced lymphatic bioavailability of curcumin of claim 14, wherein the composition comprises a surface area of about 0.17 m²/g.

18. The composition for enhanced lymphatic bioavailability of curcumin of claim 14 comprising a Scanning Electron Microscopy (SEM) image chosen from FIG. 5B, FIG. 6B, FIG. 7B or FIG. 8B.

19. The composition for enhanced lymphatic bioavailability of curcumin of claim 14 comprising a Fourier Transform Infrared (FTIR) spectra as presented in FIG. 9B.

20. The composition for enhanced lymphatic bioavailability of curcumin of claim 14 comprising a Nuclear Magnetic Resonance (NMR spectra) as presented in FIG. 10B.

21. The composition for enhanced lymphatic bioavailability of curcumin of claim 14 comprising a Matrix-Assisted Laser Desorption/Ionization Time-of-Flight (MALDI TOF) spectra as presented in FIG. 11B.

22. The composition for enhanced lymphatic bioavailability of curcumin of claim 14, wherein the essential oil of turmeric comprises ar-turmerone.

23. The composition for enhanced lymphatic bioavailability of curcumin of claim 14, wherein the essential oil of turmeric comprises about 30% to about 60% ar-turmerone by weight.

24. The composition for enhanced lymphatic bioavailability of curcumin of claim 14, wherein a weight ratio of the curcuminoid mixture to the essential of turmeric ranges from about 5:1 to about 20:1 by weight.

25. An oral dosage form comprising the composition for enhanced lymphatic bioavailability of curcumin of claim 14 chosen from tablet, capsule, soft gel capsule, granule, powder, lozenge, syrup, elixir, solution or suspension.

26. The composition for enhanced lymphatic bioavailability of curcumin of claim 14 prepared by a method, the method comprising:
- suspending a curcuminoid mixture in about 10 to about 20 times water to form a suspension;
- refluxing the suspension at about 70° C. to about 95° C. for about 0.5 hour to about 5 hrs to obtain a refluxed mixture;
- evaporating water from the refluxed mixture under vacuum and at about 30° C. to about 60° C. till volume of the refluxed mixture is decreased to half to obtain an evaporated mixture;
- adding essential oil of turmeric to the evaporated mixture to form a blend;
- drying the blend under vacuum at about 30° C. to about 65° C. to obtain the composition for enhanced lymphatic bioavailability of curcumin of claim 14.

* * * * *